United States Patent [19]

Buese et al.

[11] Patent Number: 5,298,589

[45] Date of Patent: Mar. 29, 1994

[54] HIGHLY FUNCTIONALIZED POLYCYCLOSILOXANES AND THEIR POLYMERIZATION INTO THERMALLY REVERSIBLE LIVING RUBBERS

[75] Inventors: Mark A. Buese, Upper Darby; Pao-Sun Chang, Philadelphia, both of Pa.

[73] Assignee: Temple University-Of The Commonwealth System of Higher Education, Philadelphia, Pa.

[21] Appl. No.: 915,487

[22] Filed: Jul. 16, 1992

[51] Int. Cl.$^5$ .............................................. C08G 77/08
[52] U.S. Cl. ....................... 528/21; 528/23; 528/37; 525/477
[58] Field of Search ..................... 528/21, 23, 37; 556/460; 525/477

[56] References Cited

U.S. PATENT DOCUMENTS

| 2,793,222 | 5/1957 | Kantor et al. | 260/448.2 |
| 3,465,020 | 9/1969 | Frye | 260/448.8 |
| 3,629,359 | 12/1971 | Nitzsche et al. | 260/825 |
| 3,706,591 | 12/1972 | Nitzsche et al. | 528/37 |
| 4,826,710 | 5/1989 | Buese | 427/387 |

OTHER PUBLICATIONS

Frye, *J. Org. Chem.*, 349(9), 2496-9 (1969).
Kipping et al., *J. Chem. Soc.* 81-84 (1944).
Gilbert and Kantor, *J. Polym. Sci.* 40, 35-38 (1959).
Mayo et al., *J. Plymer Sci.* 55, 65 (1961).
Andrianov et al., *Izv. Akad. Nauk SSSR, Ser. Khim* 1975, 9, 2055-8.
Soucek et al., *Dokl. Akad. Nauk SSSR*, 1976, 227(1), 98-100.
Andrianov et al., *Vysokomol. Soyed.*, 1977, A19(1) 76-9.
Zhdanov et al., *Izv. Akad. Nauk SSSR, Ser. Khim.* 1984, (8) 1851-6.
Chem. Abstract 87:6072t (1977), abstracting Andrianov et al., *Izv. Akad. Nauk SSR., Ser. Khim.* (2) 410-13, 1977.
Chem. Abstract 85:5753n (1976), abstracting Andrianov et al., *Sobshch. Akad. Nauk. Gruz. SSR* 81(2), 349-52 (1976).
Noll, *Chemistry and Technology of Silicones*, p. 3 1968.

*Primary Examiner*—John C. Bleutge
*Assistant Examiner*—Margaret W. Glass
*Attorney, Agent, or Firm*—Seidel, Gonda, Lavorgna & Monaco

[57] ABSTRACT

A composition curable to a thermally reversible rubber comprises (i) a strong acid catalyst having a $pK_a$ of less than about $-9$, (ii) at least one polycyclosiloxane containing at least one polyfunctional siloxane unit, and (iii) at least one polysiloxane selected from the group consisting of a linear polydimethylsiloxane; a polydimethylcyclosiloxane containing from about 6 to about 50 silicon-oxygen bonds; a linear or cyclic block copolymer of polydimethylsiloxane and a non-siloxane organic polymer; and a linear or cyclic random copolymer of a siloxane of the formula $Si(R)(R^1)O$ wherein R and $R^1$ are different and are selected from the group consisting of hydrogen, $C_1$–$C_{18}$ hydrocarbon and $C_2$–$C_{18}$ hydroxyalkyl, wherein the catalyst comprises from about 0.05 to about 0.5 wt % of the composition, and the concentration of polyfunctional siloxane units is at least about two times the catalyst concentration in the composition, but no more than about 0.27 molar. Novel compounds useful as the polycyclosiloxane component of the composition are also provided.

70 Claims, No Drawings

HIGHLY FUNCTIONALIZED POLYCYCLOSILOXANES AND THEIR POLYMERIZATION INTO THERMALLY REVERSIBLE LIVING RUBBERS

FIELD OF THE INVENTION

The invention relates to highly functional polycyclosiloxanes and the polymerization thereof into networks forming thermally reversible rubbers which exhibit "living" behavior.

BACKGROUND

Thermally reversible networks were reported by Frye, J. Org. Chem., 34 (9), 2496–9 (1969) for the base catalyzed ring-opening polymerization of spirocyclotetraalkoxysilanes. The thermal reversibility was attributed to the relatively high stability of the spirosiloxane rings, that is, the polymerization exhibited a positive enthalpy and a positive entropy. The network was not a rubber since the cross-linking density was too high. In other spiroalkoxysilane systems, thermally reversibility was not observed. See, e.g., Kipping et al., J. Chem. Soc. 81–84 (1944). The spriosiloxanes are generally difficult to prepare in high yield.

U.S. Pat. No. 2,793,222 (Kantor et al.) describes the production of organopolysiloxane elastomers by incorporating into a polymerizable organopolysiloxane mixture the cross-linker 1,2-bis-heptamethylcyclotetrasiloxanylethane ("ditetramer"), which is a dimer of octamethylcyclotetrasiloxane. The acid catalysts described by Kantor et al., ferric chloride and sulfuric acid, are too weak to result in formation of a living rubber.

Bis-heptamethylcyclotetrasiloxane-yl-methane and bis-heptamethylcyclotetrasiloxane-yl-ethane were prepared by Gilbert and Kantor, J. Polym. Sci. 40, 35–38 (1959), by the action of peroxides on octamethylcyclotetrailoxane. The resulting yield was poor and the only cross-linking functionality which may result is tetrafunctional. Networks could be prepared, but thermal reversibility was not reported. The copolymerization of ditetramer in the presence of a base catalyst, tetra-n-butylphosphonium hydride is described. A base catalyst will not result in formation of a living rubber.

Mayo et al., J. Polymer Sci. 55, 65 (1961) discloses a tetrafunctional cross-linker which, under the appropriate conditions, could result in living rubber formation. However, the reference recites polymerization in the presence of a base catalyst. A living rubber therefore did not result.

An improved synthesis for certain polycyclosiloxanes via hydrosilation chemistry was later reported. For example, the trifunctional polycyclosiloxane1,3-di-(2-heptamethylcyclosiloxane-yl-ethyl)-1,1,3,3-tetramethyldisiloxane was prepared in high yield and purity from vinylheptamethylcyclotetrasiloxane and tetramethyldisiloxane (Andrianov et al., Izv. Akad. Nauk SSSR. Ser. Kim., 1975, 9, 2055–8). The polymerization of this compound and its use as a cross-linker in a rubber composition are unreported.

U.S. Pat. No. 4,826,710 (Buese) describes bicyclosiloxane imides which may be cured in the presence of an acid catalyst to a hard network, or optionally cured with a cyclic siloxane to effect the formation of a flexible network. Living behavior was not reported since the networks were too highly cross-linked.

SUMMARY OF THE INVENTION

It is an object of the invention to provide vulcanizable rubbers that, due to their living behavior, are thermally reversible.

It is an object of the invention to provide novel polycyclosiloxanes which may be used as components to form such networks, by furnishing cross-linking sites of predetermined functionality to the resulting network upon cure.

It is an object of the invention to provide for the preparation of silicone networks by methods that permit the formation of a specific predetermined final structure determined solely by the composition of preformed bifunctional and polyfunctional units included in a pregel state.

It is an object of the invention to provide a versatile method for rubber preparation by reacting a polysiloxane and polycyclosiloxane such that the structure, and hence the material properties of the resulting rubber, may be varied over a wide range by the appropriate choice and proportion of reactants.

These and other objects will be apparent from the following disclosure.

As used herein, the term "polyfunctional siloxane unit" is meant a discrete segment of a polycyclosiloxane molecule consisting of silicon, oxygen and carbon atoms connected in such a fashion that the unit contains at least three Si—O groups which are connected via a backbone of Si—C bonds, C—C bonds and/or C—O bonds such that no hydrolyzable or redistributable chemical groups are included in the backbone. As a consequence, when a polycyclosiloxane containing a polyfunctional unit so defined is induced to undergo Si—O bond redistribution, the silicon atoms of the polyfunctional unit which are responsible for forming reactive bonds with oxygen can not diffuse from one another.

By "thermally reversible rubber" is meant a composition which, upon heating to a critical temperature which depends on the structure of the rubber, displays liquid behavior, and upon cooling, reverts to the original rubber state. The rubber may be repeatedly heated to a liquid and cooled to a solid rubber.

In one embodiment, the invention is a process and composition for preparing a thermally reversible rubber. The composition is a mixture comprising a polycyclosiloxane as a cross-linker, a polysiloxane, a polymerization catalyst, and optional filler.

The process comprises reacting such a mixture comprising a strong acid catalyst having a $pK_a$ of less than about −9, at least one polycyclosiloxane containing at least one polyfunctional siloxane unit, and at least one polysiloxane selected from the group consisting of

- linear polydimethylsiloxane,
- polydimethylcyclosiloxane containing from about 6 to about 50 silicon-oxygen bonds,
- linear or cyclic block copolymer of polydimethyl siloxane and a non-siloxane organic polymer, and
- linear or cyclic random copolymer of a siloxane of the formula $Si(R)(R^1)O$ wherein R and $R^1$ are different and are selected from the group consisting of hydrogen, $C_1$-$C_{18}$ hydrocarbon and $C_2$-$C_{18}$ a hydroxyalkyl, wherein the catalyst comprises from about 0.05 to about 0.5 wt % of the reaction mixture, and the concentration of polyfunctional siloxane units contributed by the polycyclosiloxane to the reaction mixture is at least about two times the catalyst concentration in the reaction mixture, but no more than about 0.27 molar.

Preferably, the catalyst comprises from about 0.1 to about 0.4 wt. % of the reaction mixture. The reaction mixture preferably contains at least one polycyclosiloxane having a tetrafunctional or higher functionality polyfunctional siloxane unit, more preferably a pentafunctional or higher functionality polyfunctional siloxane unit. According to a preferred embodiment, the reaction mixture comprises, on a weight percent basis, about 50-99.5% of the polysiloxane, about 0.25-50 wt. % of the polycyclosiloxane, and about 0.05-0.5 wt. % catalyst. The composition may also comprise optional ingredients, principally fillers compatible with the acid catalyst.

In another embodiment, the invention is directed to a series of novel polycyclosiloxanes useful as crosslinking agents for preparing thermally reversible rubbers.

DETAILED DESCRIPTION OF THE INVENTION

The present invention is directed to the preparation of silicone networks by methods that permit the formation of a specific predetermined final structure determined solely by the compositon of preformed difunctional and polyfunctional units included in a pregel state. The process involves the living ring-opening copolymerization of polycyclosiloxanes and polysiloxanes, most notably, cyclosiloxanes. All chainlink units of the polycyclosiloxane, except for those that define the functionality of the cross-links, are sites for disproportionation of the network. When such networks are formed using reactants with a very small ratio of polyfunctional to difunctional units, in the presence of a very active acid catalyst, the rubbers that are formed behave in a living manner. The rubbers are observed to grow when fed with monomer, are self-healing, and may be "killed" by adding reagents to inactivate the catalyst. Such compositions are observed to flow readily at elevated temperatures, acting as thermally reversible gels.

The polycyclosiloxanes used in the process of the present invention contain polyfunctional siloxane units which serve as linking groups which become cross-linking sites for network formation. The polyfunctional siloxane units contain at least 3, and as many as 8 or more, Si—O bonds which are interconnected by a common backbone consisting of silicon-carbon, carbon-carbon and/or carbon-oxygen bonds exclusively. These Si—O bonds are reactive, forming sites available for crosslinking. The number and functionality of the cross-link sites of the network may be predetermined and controlled by the proportion of polycyclosiloxane and polysiloxane "monomers" used as the network-forming reactants. The network may be prepared at room temperature, in the presence of a strong acid. The network is thermally reversible. It may be heated and melted. Upon cooling, the structure returns to its initial rubbery state. The network results in the formation of a truly "living" rubber. Tears or other defects in the rubber heal upon standing. The healing process may be accelerated by heating. In the cooled state, the structure is dimensionally stable and insoluble in common solvents for silicones.

The silicone networks prepared according to the present invention are thermally reversible due to the living nature of the active site of siloxane redistribution from which the network is produced.

The polysiloxane component may comprise, for instance, a linear polydimethylsiloxane, more particularly a linear polydimethylsiloxane $CH_3(—Si(CH_3)_2O—)_nCH_3$ wherein n is from about 100 to about 10,000,000, preferably from about 1,000 to about 1,000,000, most preferably from about 10,000 to about 100,000. The polysiloxane component may likewise comprise a polydimethycyclosiloxane, more particularly a polydimethylcyclosiloxane $(—Si(CH_3)_2O—)_m$, wherein m is from about 3 to about 25, preferably from about 4 to about 12. The polysiloxane component may yet also comprise a linear or cyclic block copolymer of the aforementioned polydimethylsiloxanes and a non-siloxane organic polymer such as, for example, polyalkylene, polyarylene, polyester, polyether, polyamide, polyimide, polyurethane and polyurea. The ratio of dimethylsiloxy monomer units $—Si(CH_3)_2O—$ to non-dimethylsiloxy monomer units in the block copolymer may range, for example from about 1:1 to about 100,000:1, preferably from about 5:1 to about 10,000:1, most preferably from about 10:1 to about 1,000:1. The polysiloxane may further comprise a linear or cyclic random copolymer of a siloxane of the formula $Si—(R)(R^1)O$ wherein R and $R^1$ are different and are selected from the group consisting of hydrogen, $C_2$-$C_{18}$ hydroxyalkyl, and $C_1$-$C_{18}$ straight or branched chain alkyl, alkenyl or alkynyl. The polysiloxane component may comprise a mixture of two or more of any of the aforementioned species polysiloxanes.

The polycyclosiloxane component may comprise any polycyclosiloxane containing at least one polyfunctional siloxane unit. A polycyclosiloxane containing only difunctional units, and no tri- or higher-functionality units, yields viscous fluids, but not networks. A trifunctional siloxane unit comprises a chemical unit characterized by the presence of three Si—O groups which are interconnected via a backbone of Si—C bonds, C—C bonds and/or C—O bonds such that no hydrolyzable or redistributable chemical groups are included in the backbone. As a consequence, when a polycyclosiloxane containing a polyfunctional unit so defined is induced to undergo Si—O bond redistribution, the silicon atoms of the polyfunctional unit which are responsible for forming reactive bonds with oxygen can not diffuse from one another. The polycyclosiloxanes donate a cross-linking site that will be present in the final equilibrium network structure. The number of sites that have functionalities that differ from those contained in the polycyclics should be small, consisting of the few sites which have two arms attached as a cyclic rather than being connected to a second cross-linking site, or arms which are capped by acidolysis products. Since all Si—O bonds in the networks are potential reaction sites, the active centers can freely percolate through the entire network, resulting in complete reaction and yielding a minimum energy structure. This final structure should exhibit branches between cross-links whose average size depends only upon the proportion of polyfunctional units and difunctional units fixed by the initial composition. The size distribution of branches between cross-linking sites should be a Flory-Shultz distribution. The sol in equilibrium with the network structure should be composed exclusively of cyclosiloxanes whose composition fits that observed experimentally, when corrected for the small proportion bound to cross-linking sites.

The polycyclosiloxanes useful in the practice of the present invention include, for example, the compounds according to any of formulae (I) through (VI),

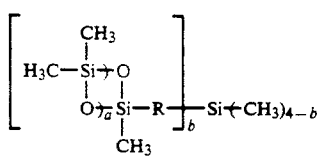
(I)

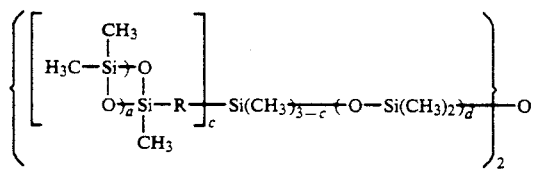
(II)

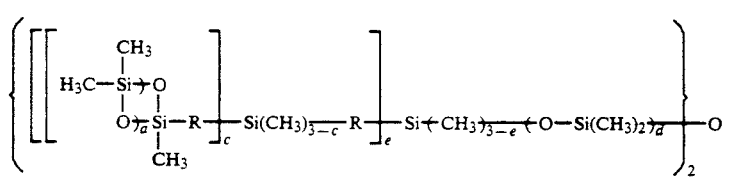
(III)

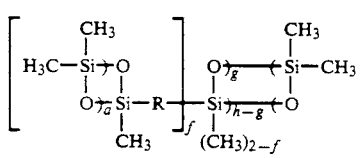
(IV)

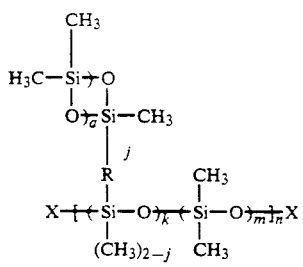
(V)

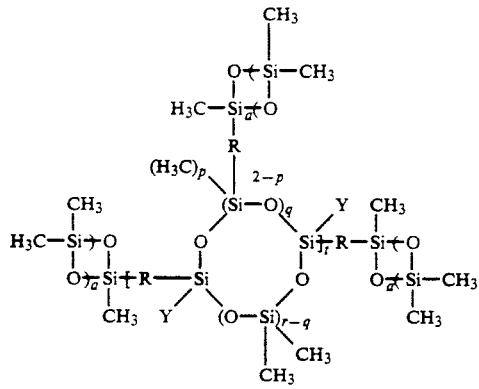
(VI)

wherein
each R, same or different, is selected from the group consisting of oxygen and $C_1$ to $C_{12}$ alkylene, preferably $C_2$ to $C_8$ alkylene, most preferably $C_2$ alkylene;
a is from 2 to 20, preferably 2 to 8, most preferably 3;
b is 2, 3 or 4;
c is 1, 2 or 3;
d is zero to 100;
e is 1, 2 or 3;
f is 1 or 2;
g is 1 to h;
h is 3 to 20, preferably 3 to 8, most preferably 4;
j is 1 or 2;
m is 1 to 100;
X is hydrogen, $C_1$ to $C_{12}$ straight or branched chain alkyl, $C_1$ to $C_{12}$ straight or branched chain alkoxy, phenyl, vinyl or Z,
wherein Z is

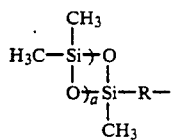

(VII)

provided that:
when X is Z:
k is 1 to 100 and
n is 1 to 100;
when X is other than Z:
k is 1 to 100 and
n is 1 to 100, except that when k is 1 or 2, n must be greater than 2, and when n is 1 or 2, k must be greater than 2;
Y is methyl or Z;
p is 1 or 2;
q is zero to r;
r is 1 to 18; and
t is zero to 100.

The compounds of formulae (I), (III) and (V) are novel. The compounds of formula (II) are novel, except for those compounds wherein a is 3 and c is 1 in the same compound. The compounds of formula (IV) are novel, except for those compounds wherein f is 1 and g is 1 in the same compound. The compounds of formula (VI) are novel, provided p is 2. If p is 1, novel compounds of formula (VI) comprise all compounds so defined, except where R is methylene or ethylene.

The novel polycyclosiloxanes thus comprise the compounds according to:
formula (I) wherein
  each R, same or different, is selected from the group consisting of oxygen and $C_1$ to $C_{12}$ alkylene, preferably $C_2$ to $C_8$ alkylene, most preferably $C_2$ alkylene;
  a is from 2 to 20, preferably 2 to 8, most preferably 3; and
  b is 2, 3 or 4;
formula (II) wherein
  R is defined as above,
  a is 2 to 20,
  c is 1 to 3, and
  d is zero to 100,
  provided a may not be 3 and c may not be 1 in the same compound;
formula (III) wherein
  R is defined as above,
  a is 2 to 20,
  c is 1 to 3,
  d is zero to 100, and
  e is 1 to 3;
formula (IV) wherein
  R is defined as above,
  a is 2 to 20,
  f is 1 or 2,
  g is 1 or h,
  h is 3 to 20,
  provided, f and g are not both 1;
formula (V) wherein
  R is defined as above,
  a is 2 to 20,
  j is 1 or 2,
  m is 1 to 100,
X is hydrogen, $C_1$ to $C_{12}$ straight or branched chain alkyl, $C_1$ to $C_{12}$ straight or branched chain alkoxy, phenyl, vinyl or Z, wherein Z is

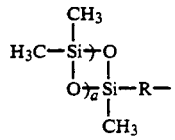

(VII)

provided that:
when X is Z:
k is 1 to 100 and
n is 1 to 100;
when X is other than Z:
k is 1 to 100 and
n is 1 to 100, except that when k is 1 or 2, n must be greater than 2, and when n is 1 or 2, k must be greater than 2;
formula (VI) wherein
R is defined as above,
a is 2 to 20,
Y is methyl or Z,
p is 1 or 2,
q is zero to r,
r is 1 to 18, and
t is zero to 100,
provided that when p is 1, R may not be $CH_2$ or $CH_2CH_2$.

In particular, the polycyclosiloxane used in preparing the thermally reversible rubbers may be: 1,3-di-(2-heptamethylcyclotetrasiloxane-yl-ethyl)-1,1,3,3-tetramethyldisiloxane, the preparation of which is disclosed by Andrianov et al., Izv. Akad. Nauk SSSR. Ser. Kim.. 9, 2055-8 (1975)); 1,2-bis-(heptamethylcyclotetrasiloxane-yl)-ethane, the preparation of which is disclosed in U.S. Pat. No. 2,793,222 (Kantor et al.); bis-(heptamethylclotetrasiloxane-yl)-dimethylsilane; 1,3,5,7-tetra-(2-heptamethylcyclotetrasiloxane-yl-ethyl)-1,3,5,7-tetramethylcyclotetrasiloxane; 1,1,3,3-tetra-(2-heptamethylcyclotetrasiloxane-yl-ethyl)-1,3-dimethyldisiloxane; tris-(heptamethylcyclotetrasiloxane-yl)-methylsilane; hexa-(2-heptamethylcyclotetrasiloxane-yl-ethyl)-disiloxane; 1,3-di-{2-[tri-(2-heptamethylcyclotetrasiloxane-yl-ethyl)]-silylethyl)}1,1,3,3-tetramethyldisiloxane; tetrakis-(heptamethylcyclotetrasiloxane-yl)-silane; polydimethylsiloxanes which are end capped with: (2-heptamethylcyclotetrasiloxane-yl-ethyl)-dimethylsiloxy-, di-(2-heptamethylcyclotetrasiloxane-yl-ethyl)-methylsiloxy-, tri-(2-heptamethylcyclotetrasiloxane-yl-ethyl)-siloxy-, {2-[di-(2-heptamethylcyclotetrasiloxane-yl-ethyl)-methylsilyl]-ethyl}-dimethylsiloxy-, {2-[-tri-(2-heptamethylcyclotetrasiloxane-yl)-silyl]-ethyl}-dimethylsiloxy-, bis-{2-[di-(2-heptamethylcyclotetrasiloxane-yl-ethyl)methylsilyl]-ethyl}-methylsiloxy-, bis-(2-[tri-(2-heptamethylcyclotetrasiloxane-yl-ethyl)-silyl]-ethyl}-methylsiloxy-, tris-{2-[di-(2-heptamethylcyclotetrasiloxane-yl-ethyl)-methylsilyl]-ethyl)-siloxy-; poly[2-heptamethylcyclotetrasiloxane-yl-ethyl)methylsiloxane]; poly[di-(2-heptamethylcyclotetrasiloxane-yl-ethyl)siloxane]; poly[(2-heptamethylcyclotetrasiloxane-yl-ethyl)-methylsiloxane-co-dimethylsiloxane] ; and poly[di-(2-heptamethylcyclotetrasiloxane-yl-ethyl)-siloxane-co-dimethylsiloxane].

Preferred compounds include the following, which provide from three to eight functional sites, respectively: 1,3-di(2-heptamethylcyclotetrasiloxane-yl-ethyl)-1,1,3,3-tetramethyldisiloxane(1); 1,3,5,7-tetra-(2-heptamethylcyclotetrasiloxane-yl-ethyl)-1,3,5,7-tetramethylcyclotetrasiloxane (2); 1,3,3,3-tetra-(2-heptamethylcyclotetrasiloxane-yl-ethyl)-1,3-dimethyldisiloxane (3); tris-(2-heptamethylcyclotetrasiloxane-yl-ethyl)-methylsilane (4); 1,3-di-(2-[tri-{2-heptamethylcyclotetrasiloxane-yl-ethyl)]-silylethyl}-1,1,3,3-tetramethyldisiloxane (5); and tetrakis-(2-heptamethylcyclotetrasiloxane-yl-ethyl)-silane (6). Compounds (2) through (6) are novel. In the following structures, methyl groups are indicated by lead lines from silicon. Thus, it will be understood that the dimethylsiloxy unit may appear as

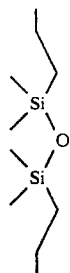

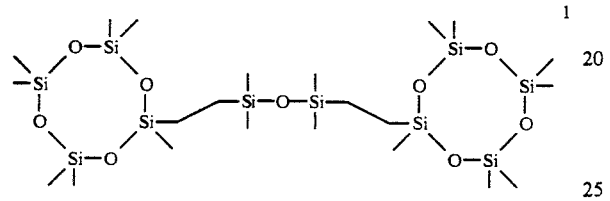
1

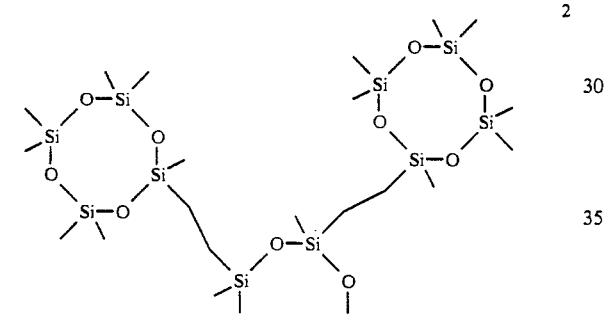
2

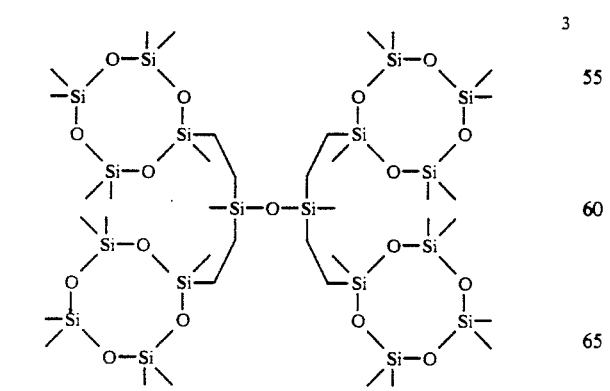
3

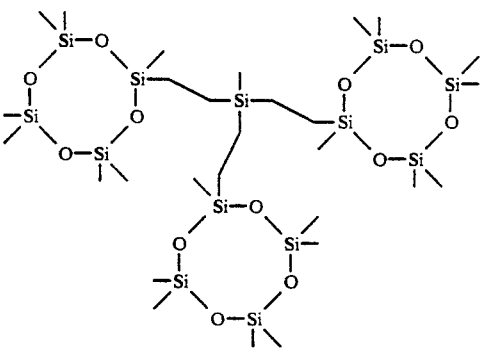
4

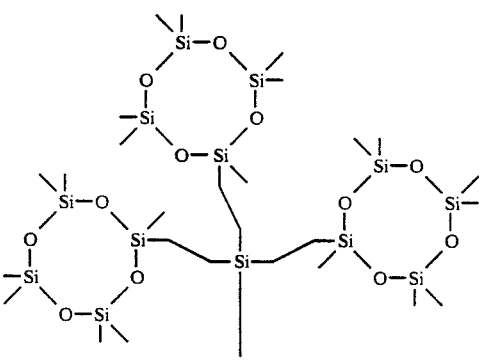
5

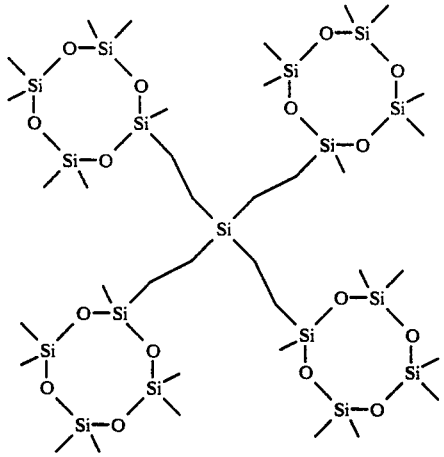

As may be appreciated from a study of formulae (I) through (VI), above, the bridging group R linking the cyclosiloxane rings to each other directly or through one or more intervening silicone atoms or siloxy units may be alkylenyl or oxygen. Where R=alkylenyl, the polycyclosiloxanes may be prepared in high yield by hydrosilation. A slight excess of a cyclosiloxane having at least one Si—H group, such as heptamethylcyclosiloxane or homologous compound of different ring size, is reacted with a silane which contains an unsaturated group, e.g., divinylsilane or polyvinylsilane, or with a siloxane containing an unsaturated group. The alkenyl-substituted siloxane may be a linear oligomer or polymer, or may be a cyclosiloxane. Conversely, an alkenyl-heptamethylcyclotetrasiloxane or homologous compound of other ring size may be reacted with a siloxane or silane containing an Si—H group. Those skilled in the art will be able to select the appropriate reactants in each case, to arrive at the desired product.

Alternatively, heptamethylcyclosiloxane or homologous compound of different ring size is chlorinated, hydrolyzed and then self-condensed, or condensed with a difunctional or polyfunctional silane such as, for example, dimethyldichlorosilane, bis-(N,N-dimethylamino)dimethylsilane, tetrakis-(dimethylamino)silane. The highest yield may be obtained when vinylheptamethylcyclosiloxane is hydrosilated with α,ω-hydrogen-oligo(dimethylsiloxanes) in the presence of a platinum catalyst. Hydrosilation reactions employing heptamethylcyclosiloxane and vinyl-containing silanes and siloxanes yield a variety of polycyclosiloxanes with various numbers of cyclosiloxane rings connected through tri-, tetra-, penta-, hexa-, hepta-, or octafunctional units. The hydrosilation reaction occurs with a regioselectivity for hydrogen addition to the α-Si carbon over the β-Si carbon of the olefin reactant to differing degrees, depending on the nature of the vinylsilane or siloxane and the Si—H-containing reagent.

The polycyclics (1) through (6) were synthesized in high yield (>85%; by the hydrosilation of 1,3-divinyl-1,1,3,3-tetramethyldisiloxane, 1,3,5,7-tetravinyl-1,3,5,7-tetramethylcyclotetrasiloxane, 1,1,3,3-tetravinyl-1,3-dimethyldisiloxane, trivinylmethylsilane, 1,3-di-(2-trivinylsilylethyl)-1,1,3,3-tetramethyldisiloxane and a tetravinylsilane with 1.1 molar excess of heptamethyltetracyclosiloxane in the presence of small amounts of (<100 ppm) platinum-divinylmethyldisiloxane complex (5% Pt). The reactions were carried out at 70° C. for one to two hours. All of the products were isolated by vacuum distillation. They were analyzed by gas chromatography, $^1$H NMR spectroscopy and vapor pressure osmometry. Rubbers were prepared using various mixtures of polycyclics and octamethylcyclotetrasiloxane where the ratio of disiloxy units to polysiloxy units ranged from 200:1 to 800:1. The concentrations of acid catalyst used were varied from 0.05 to 0.5 percent.

The polysiloxanes according to formulae (I)–(VI) in the bridging group R comprises an atom of oxygen are prepared by reacting a cyclosiloxane having at least one Si—H group, e.g., heptamethylcyclosiloxane or homologous compound of different ring size, with a silane or siloxane compound which contains two or more leaving groups such as, for example, amino, amido, halo, alkoxy or acetyl groups. If a catalyst is required, the choice of the catalyst, and acid scavenger if required, will be apparent to those skilled in the art. Those skilled in the art will be able to select the appropriate reactants in each case, to arrive at the desired product.

A preferred group of novel oxygen bridged compounds of formula (VI) are defined according to the formula (VIII) wherein x is zero or 1 and n is from 1 to 100.

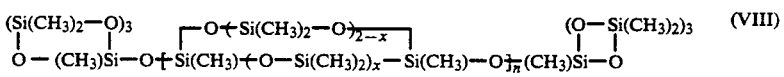

The compounds are useful as the polycyclosiloxane component in the preparation of thermally reversible rubbers.

A novel oxygen-bridged polycyclosiloxane, according to formula (I), useful in the preparation of the thermally reversible rubbers, is tetrakis-(heptamethylcyclotetrasiloxane-yl-oxy)silane (8), which has the formula:

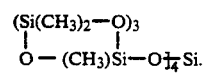

It may be appreciated, however, that where the bridging unit in the polycyclosiloxane compound is an oxygen atom, the functionality of the various polyfunctional siloxane units in the compound may be trifunctional or tetrafunctional, but not a higher functionality.

Preferably, the polycyclosiloxane contains at least one tetrafunctional or higher functionality unit, more preferably, at least one pentafunctional or higher functionality unit. The polycyclosiloxane includes two or more cyclosiloxane rings. The polycyclosiloxane is formed from a starting cyclosiloxane of any ring size. Polycyclosiloxanes containing trisiloxyl rings, however, may cure too rapidly, resulting in an initial nonhomogeneous cure. Such systems may have the further disadvantage of considerable shrinkage and heat evolution upon curing. Thus, polycyclosiloxanes wherein the ring structures comprise cyclotetramer and larger rings, particularly cyclotetramer and cyclopentamer rings, are preferred. Polycyclosiloxanes comprising cyclotetramer rings, i.e., the heptamethylcyclosiloxyl moiety, are most preferred, as illustrated by compounds 1 through 6.

The catalyst may comprise any strong acid having a $pK_s$ of lower than $-9$. Such acids include, for example, trifluoromethanesulfonic, nitrotrifluoromethylbenzenesulfonic, trifluoromethylbenzenesulfonic, pentafluorobenzenesulfonic, 2,2,2-trifluoroethylsulfonic, nitrobenzenesulfonic, dinitrobenzenesulfonic, fluorobenzenesulfonic, nitrofluorobenzenesulfonic, nitrotrifluoromethylsulfonic and benzenedisulfonic acids. Base catalysts, and acid catalysts weaker than the aforementioned very strong acid catalysts, are ineffective in providing a rubber having thermal reversibility. See Comparative Examlples 10–13, below. The preferred acid is trifluoromethane sulfonic acid.

The amount of catalyst in the reaction mixture comprising the polycyclosiloxanes, polysiloxanes and catalyst is from about 0.05 to about 0.5 wt. % of the reaction mixture. Below about 0.05 wt. %, too little acid is present, and the rate of siloxane bond redistribution is too slow for appreciable thermal reversible behavior to be observed. Above about 0.5 wt. % catalyst, the resulting network is characterized by a sticky mass, which has little or no practical uses. Furthermore, the polycyclosiloxane and catalyst concentration are selected such that the polyfunctional siloxane units contributed to the reaction mixture by the polycyclosiloxane is at least about two times the catalyst concentration in the reaction mixture, but such that the concentration of polyfunctional units does not exceed about 0.27 molar. It should be appreciated that where the polycyclosiloxane in the reaction mixture contains a single polyfunctional siloxane unit, the concentration of polyfunctional siloxane units in the reaction mixture is equal to the polycyclosiloxane concentration in the mixture. Similarly, where the polycyclosiloxane contains two polyfunctional siloxane units, the polyfunctional siloxane unit concentration is equal to two times the polycyclosiloxane concentration. Preferably, the catalyst concentration is from about 0.1 to about 0.4 wt. % of the reaction mixture.

The composition may contain optional fillers. The filler must be compatible with the catalyst, that is, it must be compatible with a strong acid catalyst. Such fillers include, for example, carbon black, graphite, glasses of all types, polymeric fibers, and neutral salts.

The intial curing behavior of the composition containing the polysiloxane and polycyclosiloxane reactants, catalyst, and optional fillers depends upon the nature, proportions, and order in which the reactants and catalyst are combined. Where the polysiloxane and catalyst are combined in the absence of the polycyclosiloxane, and the polycyclosiloxane is then subsequently added, the resulting mixture is a thick dough. The dough can be molded and shaped. In this case the rubber is latent and can be induced to form by increasing the temperature. Where the polycyclosiloxane and polysiloxane are mixed prior to the addition of the catalyst, and the catalyst is thereafter added, the thermally reversible rubber is generated directly.

When the catalyst is added last, the catalyst may be dispersed by shacking or stirring and the liquid poured into a mold or spread onto a surface to be cured.

The pre-mixed reactants and catalyst may be combined at atmospheric pressure, although greater or lesser pressures may be employed. The preferred temperature is simply the ambient temperature, such as room temperature, although higher or lower temperatures may be utilized. The temperature may be permitted to range up to the temperature of liquifaction of the composition, which is typically above 100° C. Where the catalyst and polysiloxane component are combined first, the resulting mixture should be heated at least slightly with addition of the polycyclosiloxane to overcome the glass effect which occurs upon the mixing of the catalyst and polysiloxane and to insure uniform combination of all components. The required degree of heating may be as little as 5° C. over the temperature at which the catalyst and polysiloxane were combined, or as much as 100° C. above that temperature.

The resulting rubbers are thermally reversible, that is, they may be converted between the liquid and solid state by repeated temperature cycling between, for example, about 25° C. and about 150° C. In the cooled state, the structure is dimensionally stable and insoluble in common solvents for silicones. The particular temperature at which the rubber liquifies depends principally upon the degree of crosslinking, which in turn depends upon the nature and relative amounts of the system components. Unlike prior thermally reversible rubbers, the materials prepared according to the present invention comprise a network of covalently linked subunits.

With some compositions according to the present invention, the cure occurs uniformly throughout the liquid. Other compositions result in cure from the air surface inward. These systems give very rapid cure at the air surface. The surface-cured material may be handled while the inside remains liquid. The rubber may be inflated by pumping a gas into the inside of the curing rubber. If the gas is $N_2$ or some other dry inert gas, the point of intrusion will fill with liquid and form a rubber upon contact with the air surface, resulting in an inflated bal with no entry hole. This "living" rubber ball will ultimately cure throughout the liquid.

Once formed, the "living" rubber may be processed by heating and reforming. At sufficiently warm temperatures it becomes as a viscous liquid. From this state it can be extruded. While cooling, the rubber is particularly susceptible to deformation by external forces though its rubbery state is nearly fully restored. Fine features may be formed from this state even when it is sufficiently cool that the features may be formed by hand.

The rubber is insoluble in hydrocarbons even when all of its non-filler precursors are soluble in hydrocarbon, if the number of cross-linking sites is sufficiently large and of sufficient functionality. The rubber retains its shape in boiling water. Upon being torn the resulting matched surfaces can be placed in contact and the rubber will heal such that little or no deformation of the remainder of the surfaces can be noted by visible inspection, including fine detail. Upon warming, gross tears may be healed. The external surface of the rubber can be selectively "killed". One may then heat the rubber resulting in the formation of a viscous liquid-like center encased in a thin rubber sheath.

The materials prepared according to the present invention, because of their thermal reversibility and/or living behavior, are believed useful in a wide variety of applications such as adhesives, coatings, composites, foams, impression materials, lithography materials, and molding compounds.

The practice of the invention is illustrated by the following non-limiting examples.

All vinylsilanes, vinylsiloxanes, tetramethyldisiloxane, hexamethyldisiloxane and Platinum-divinyltetramethyldisiloxane (hydrosilation catalyst) were used as obtained from Hüls Amerika. Heptamethylcyclotetrasiloxane was isolated from mixed cyclosiloxanes stripped from a trifluoromethanesulfonic acid catalyzed redistribution of poly(dimethylsiloxane) and poly(methylhydrogensiloxane) fluids (Hüls). Heptamethylcyclotetrasiloxane was isolated with purities up to 98%. Typically, mixtures of heptamethylcyclotetrasiloxane and octamethylcyclotetrasiloxane were used where the heptamethylcyclotetrasiloxane was a minimum of 80% of the mixture. Traces (<0.4%) of hexamethylcyclotetrasiloxane were also found in most mixtures. Gas chromatographic analysis was performed on a Hewlett-Packard 5890A gas chromatograph equipped with a conductivity detector. A 6 ft×⅛ in. column packed with 5% OV-101 was used with a temperature gradient from 60° to 325° C. at 10° C./min. after one minute at 60° C., and held at the maximum temperature for ten minutes. A 6 ft.×⅛ in. column packed with 5% OV-17 with a temperature gradient from 60° to 340° C. at 10° C./min. was substituted for the analysis of compound 5. Proton and carbon-13 nuclear magnetic resonance spectra were recorded using a General Electric QE 300 spectrometer, and silicon-29 spectra were recorded on a General Electric NQ 500 spectrometer. Infrared spectra were recorded on a Mattson series 4020 FTIR spectrometer. Vapor phase osmometry (VPO) was carried out on a Knauer vapor phase osmometer using hexane at 45° C., using four or five dilute solutions for each polycyclic. Since 1,3-di(2-heptamethylcyclotetrasiloxane-yl-ethyl-1,1,3,3-tetramethyldisiloxane (1) is a known compound, molecular weight 751.5864, it was used as the VPO standard for all other polycyclics.

In the following examples, peaks marked with an asterisk (*) were assigned an isomer resulting from hydrogen addition to the β-Si carbon of the olefin reactant, resulting in the isomer marked with an asterisk (*) in the reaction schemes. Two asterisks (**) indicate a minor isomer not indicated in the corresponding scheme, which isomer contains two sites of hydrogen addition to the β-Si carbon of the olefin.

EXAMPLE 1

Preparation of 1,3-Di(2-heptamethylcyclotetrasiloxane-yl ethyl)-1,1,3,3-tetramethyldisiloxane (1)

A 50 ml round-bottomed flask equipped with a reflux condenser was charged with 20g of heptamethylcyclotetrasiloxane which contained 8% octamethylcyclotetrasiloxane (65 mmol), 6.0 g of 1,3-divinyl-1,1,3,3-tetramethyldisiloxane (32 mmol) and 40 μL of platinum-divinyltetramethyldisiloxane complex (5% Pt). The mixture was stirred and heated to 70° C. After 10 minutes the mixture displayed a slight yellow color, and gas chromatographic analysis indicated complete conversion of the starting olefin (Scheme I). An isolated yield of 23.1 g (96%) of 1 was obtained by distillation at 100° C. and 0.02 mmHg. $^1$H NMR 300 MHz, CDCl$_3$:δ 0.089 (s 12H), 0.117 (s 6H), 0.135 (s 36H), 0.450 (s 7.8 H), 1.110* (d 0.2,H). $^{13}$C NMR 75 MHz, CDCl$_3$:δ −1.675 (CH$_3$), −0.422 (CH$_3$), 0.714 (CH$_3$), 7.636* (CH$_2$), 8,494 (CH$_2$), 9.359 (CH$_2$), 11.449* (CH). $^{29}$Si NMR 99.4 MHz, CDCl$_3$ with Cr(acac)$_3$:δ−19.40, 8.25.IR (neat liquid on NaCl): cm$^{-1}$ 2962(s); 2900(s), 2875(m), 2800(w), 1900(w), 1700(W), 1609(m), 1560(m), 1445(w), 1405(s), 1261(s), 1138(s), 1075(s), 800(s), 750(s), 725(w), 700(s), 659(w), 637(w), 550(s). C$_{22}$H$_{62}$Si$_{10}$O$_9$ calc. C 35.16, H 8.31, Si 37.37, O 19.16; found C 34.78, H 8.51.

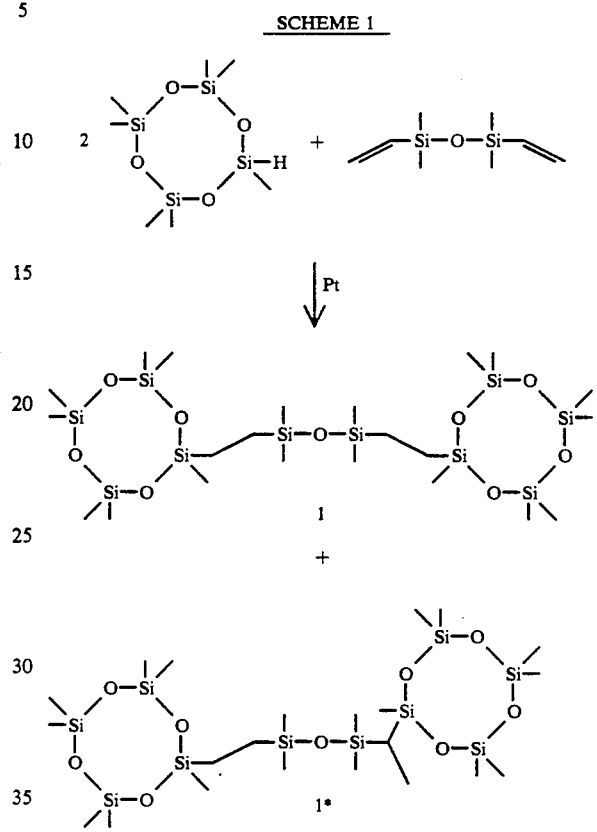

SCHEME 1

EXAMPLE 2

Preparation of 1,3,5,7-Tetra(2-heptamethylcyclotetrasiloxane-yl-ethyl)-1,3,5,7-tetramethylcyclotetrasiloxane (2)

A 50 ml round bottomed flask equipped with a reflux condenser was charged with 20 g of heptamethylcyclotetrasiloxane which contained 8% of octamethylcyclotetrasiloxane (65 mmol), 5.6 g of 1,3,5,7-tetravinyl-tetramethylcyclotetrasiloxane (16 mmol) and 40 μL of platinum-divinyltetramethyldisiloxane complex (5% Pt) as catalyst. The mixture was stirred and heated at 70° C. After 10 minutes the mixture displayed a slight yellow color which indicated the complete conversion of the starting olefin (Scheme 2). The unreacted heptamethylcyclotetrasiloxane and octamethylcyclotetrasiloxane were removed by vacuum distillation. An isolated yield of 19.68 g (82%) of the desired product, compound 2, was obtained by distillation at 198°–205° C. at <0.01 mmHg. It was pure as indicated by a gas chromatographic analysis. $^1$H NMR 300 MHz, CDCl$_3$:δ 0.114(s 96H), 0.489 (s 14.56 H), 1.070* (d 1.44 H). $^{13}$C NMR 75 MHZ, CDCl$_3$:δ−1.658 (CH$_3$), −1.563 (CH$_3$), −0.070, 0.762 (CH$_3$), 7.263* (CH$_3$), 8.238 (CH$_2$), 10.943* (CH). $^{29}$Si NMR 99.4 MHz, CDCl$_3$, with Cr(acac)$_3$:δ−19.24, −19.18 IR (neat liquid on NaCl): cm$^{-1}$ 2962(s), 2900(s), 2875(m), 2800(w), 1900(w), 1555(m), 1405(s), 1265(s), 1145(w), 1065(s), 803(s), 700(s), 659(w), 640(w), 625(w), 550(s). C$_{40}$H$_{112}$Si$_{20}$O$_{20}$ calc C 32.57, H 7.65, Si 38.08, O 21.69; found C 32.41, H 7.40. Molecular weight calc. 1,475,0328; observed VPO I, 1,490.

SCHEME 2

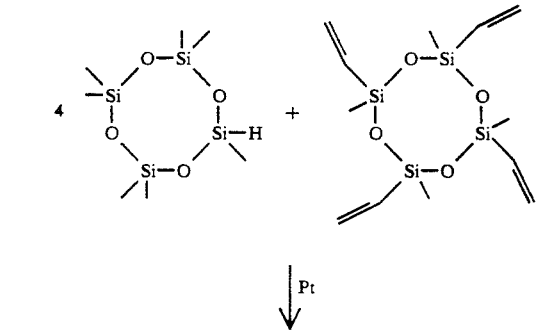

2
+

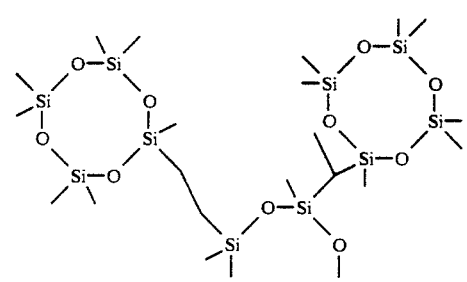

-continued
SCHEME 2

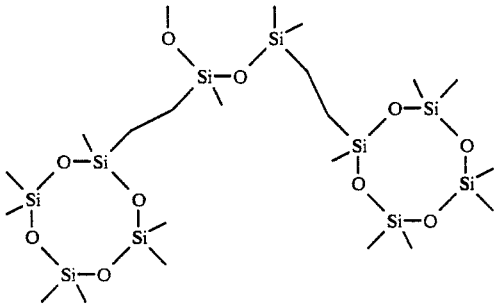

2*

EXAMPLE 3

Preparation of 1,1,3,3-Tetra(2-heptamethylcyclotetrasiloxane-yl-ethyl)-1,3-dimethyldisiloxane (3)

A 25 ml round bottomed flask equipped with a reflux condenser was charged with 6 g of 95% pure heptamethylcyclotetrasiloxane (21 mmol) and 1.05 g of 1,1,3,3-tetravinyl-1,3-dimethyldisiloxane. The mixture was stirred until it became homogeneous and 10 μL of a platinum-divinyltetramethyldisiloxane complex (5% Pt) was added to the mixture. The mixture was stirred and heated at 70° C. until it turned yellow. An aliquot was removed which indicated complete conversion of the starting olefin by IR and gas chromatography. (Scheme 3). Compound (3) was obtained by distillation at 168° C. and 0.02 mm Hg. $^1$H NMR 300 MHz, CDCl$_3$:δ 0.100 (s), 0.110 (s 90H), 0.469 (m 14.40H), 1.060* (d 1.60H). $^{13}$C NMR 75 MHz, CDCl$_3$:δ−2.628 (CH$_3$) −1.626 (CH$_3$), −1.214*, 0.762 (CH$_3$), 7.218 (CH$_2$), 7.576* (CH$_2$), 7.810* (CH$_2$), 8,492 (CH$_2$), 9.434**, 10,402* (CH), 10.797**. $^{29}$Si NMR 99.4 MHz, CDCl$_3$ with Cr(acac)$_3$:δ−19.35, −19.29, 8.82. IR (neat liquid on NaCl): cm$^{-1}$ 2962(s), 2900(s), 2875(m), 1900(w), 1694(w), 1609(m), 1550(m), 1445(w), 1405(s), 1255(s), 1125(w), 1070(s), 850(W), 800(s), 750(W), 694(s), 661(W), 644(w), 610(w), 550(s). C$_{38}$H$_{106}$Si$_{18}$O$_{17}$ calc. C 34.04, H 7.97, Si 37.71, O 20.29; found C 33.61, H 7.75. Molecular weight calc. 1,340.7932, observed (VPO) 1,300.

SCHEME 3

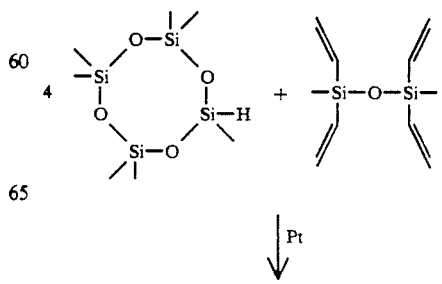

SCHEME 3 -continued

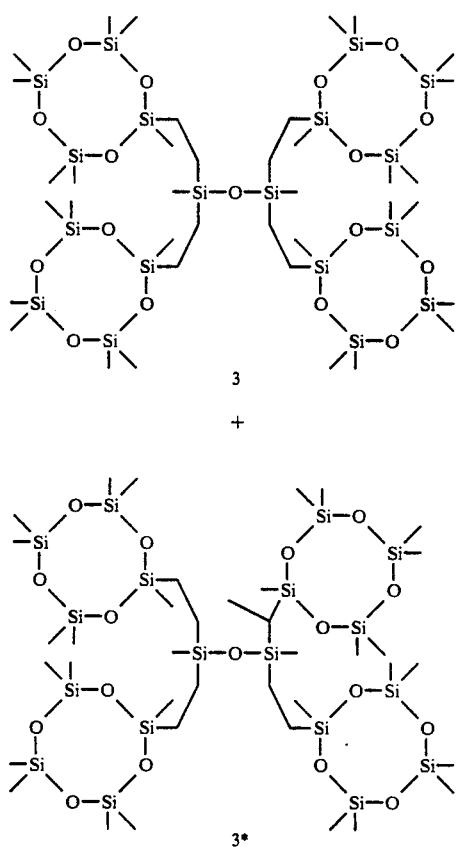

EXAMPLE 4

Preparation of Tris-(2-heptamethylcyclotetrasiloxane-yl-ethyl)methylsilane (4)

A 25 ml round bottomed flask equipped with a reflex condenser was charged with 10 g of 92% pure heptamethylcyclotetrasiloxane (33 mmol), 1.4 g of trivinylmethylsilane (11 mmol) and 0.02 g of platinum-divinyltetramethyldisiloxane (5% Pt). The mixture was stirred and heated at 70° C. until it turned yellow. An aliquot was removed which indicated complete conversion of the starting olefin by IR and gas chromatography (Scheme 4). Distillation at 125° C. and 0.02 mmHg yielded 9.75 g (92%) of compound 4. $^1$H NMR 300 MHz, CDCl$_3$:δ −0.082 (s 3H), :101 (s66H), 0.444 (s 11.2H), 1.025 (d 0.6H). $^{13}$C NMR 75 MHZ, CDCl$_3$:δ −6.709 (CH$_3$), −6,021* (CH$_3$), −1.636 (CH$_3$), 0.767 (CH$_3$), 3.700 (CH$_2$), 4.149* (CH$_2$), 5.565*, 8.431*, 9.038 (CH$_2$), 9.191* (CH$_2$). $^{29}$Si NMR 99.4 MHz, CDCl$_3$ with Cr(acac)$_3$:δ −19.40, −19.32, 8.08. IR (neat liquid on NaCl): cm$^{-1}$ 2962(s); 2900(s), 2875(m), 2795(w), 1905(w), 1700(w), 1609(m), 1550(m), 1450(W), 1405(s), 1255(s), 1138(s), 1070(s), 800(s), 750(s), 725(w), 700(s), 695(m), 653(w), 637(w), 550(s). C$_{28}$H$_{78}$Si$_{13}$O$_{12}$ calc. C 34.60, H 8.09, Si 37.56, 0 19.75; found C 34.45, H 7.80. Molecular weight calcu. 972.0350, observed (VPO) 991.

SCHEME 4

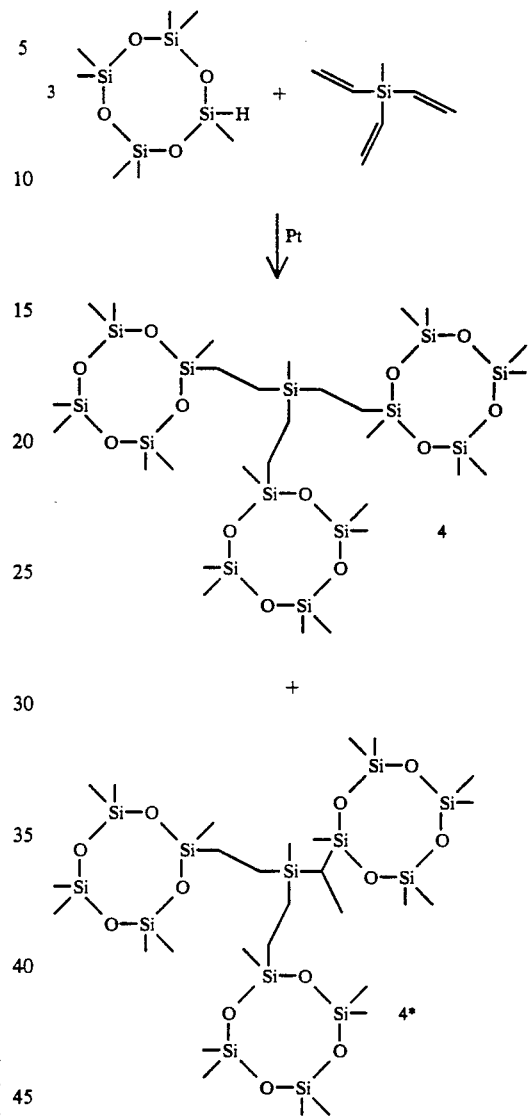

EXAMPLE 5

Preparation of 1,3-Di-{2-[tri-(2-heptamethylcyclotetrasiloxane-yl-ethyl)]silylethyl}-1,1,3,3-tetramethyldisiloxane (5)

A. 1,3-Di-[2-(trivinylsilyl)ethyl]-1,1,3,3-tetramethyldisiloxane (7)

To the 25 ml round bottomed flask equipped with a reflex condenser was charged 10.17 g of tetravinylsilane (75 mmol), 1 g of 1,1,3,3-tetramethyldisiloxane (7.5 mmol) and 10 μL of platinum-divinylmethyldisiloxane (5% Pt). The mixture was stirred and heated at 70° C. until it turned light yellow. (Scheme 5). From this mixture, 0.88 g (29% yield) of 1,3-di-[2-(trivinylsilyl)ethyl]-1,1,3,3-tetramethyldisiloxane (7) was isolated by distillation at 115° C. and 0.1 mm Hg. $^1$H NMR 300 MHz, CDCl$_3$:δ 6.22 (AXY,J$_{AX}$=18 Hz, J$_{AY}$=2 Hz Z.Z H), 6.20 (AXY, J$_{AX}$=18 Hz, J$_{AY}$=2 Hz), 6.15 (AXY,-J$_{AX}$=$^{18}$Hz, J$_{AY}$=2 Hz), 6.12 (AXY,J$_{AX}$=7 Hz, J$_{AY}$=2

Hz), 6.11* (AXY, J_{AX}=7 Hz, J_{AY}=2 Hz), 6.08 (AX-Y,J_{AX}=7 Hz, J_{AY}=2 Hz), 6.07 (AXY,J_{AX}=7 Hz, J_{AY}=Hz), 5.82** (AXY,J_{AX}=18 Hz, J_{AY}=7 Hz), 5.80* (AXY,J_{AX}=18 Hz, J_{AY}=7 Hz), 5.79 (AXY,J_{AX}=18 Hz, J_{AY}=7 Hz), 5.76** (AXY,J_{AX}=18 Hz, J_{AY}=7 Hz), 5.75* (AXY,J_{AX}=18 Hz, J_{AY}=7 Hz), 1.09** (d, 0.1 H), 1.07* (d,1.5H), 0.67 (m 1.2H), 0.47 (m 1.2 (H), 0.12* (m, 0.1H), 0.08* (s, 1H), 0.06* (s, 1H), 0.05 (s, 5H). $^{13}$NMR 75 MHz, CDCl$_3$:δ 135.089*, (CH); 134,628, (CH); 134,4, (CH$_2$); 10.137, (CH$_2$); 6.869*, (CH); 4.21*, (CH$_2$); 4.131, (CH$_2$); 1.347*, (CH$_3$); −0.34, (CH$_3$). $^{29}$Si NMR 99.4 MHz, CDCl$_3$ with Cr(acac)$_3$δ−18.12, 8.00. IR (neat liquid on NaCl): cm$^{-1}$ 3180(w), 3050(s), 3010(m), 2960(s), 2910(m), 2880(m), 2790(w), 1610(m), 1400(s), 1250(s), 1130(s), 1050(s), 1010(s), 955(s), 840(s), 800(m), 770(s), 730(s), 625(W), 550(m), 525(m). C$_{20}$H/$_{38}$Si$_4$O calc. C 59.04, H 9.41, Si 27.61, 0 3.96; found C 57.76, H 9.02.

SCHEME 5

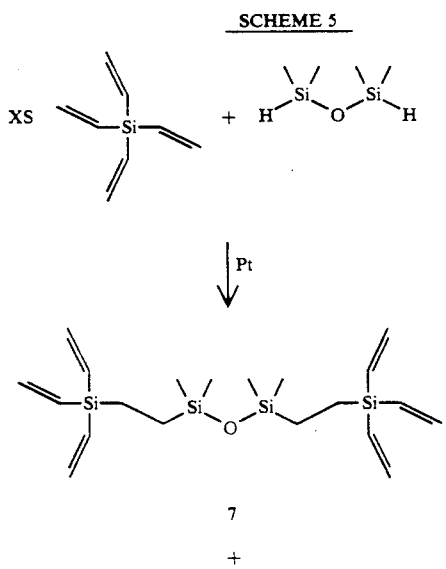

7
+

-continued
SCHEME 5

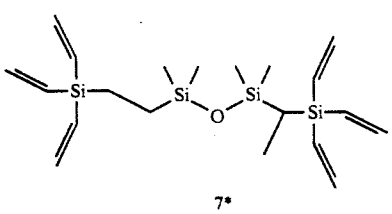

7*

B.
1,3-Di-{2-[tri-(2-heptamethylcyclotetrasiloxane-yl-ethyl)]silylethyl}-1,1,3,3-tetramethyldisiloxane (5)

To 0.5 g of 1,3-di-[2-(trivinylsilyl)ethyl]-1,1,3,3-tetramethyldisiloxane (1.4 mmol) was added 3.57 g of heptamethylcyclotetrasiloxane (9.4 mmol) and 10 μL of platinum-divinyltetramethyldisiloxane in a 10 ml round bottomed flask. The mixture was heated at 70° C. for 1 hour. An aliquot was removed which indicated complete conversion of the starting olefin by gas chromatography (Scheme 6). The unreacted heptamethylcyclotetrasiloxane was removed by distillation at 252°-6° C. and <0.01 mmHg, yielding 2.49 g (85% yield) of compound 5. $^1$H NMR 300 MHz, CDCl$_3$:δ 0.113 (s 84H), 0.450 (s 14.7H), 1.038* (d 1.3H). $^{13}$C NMR 75 MHz, CDCl$_3$:δ−1.639 (CH$_3$), −1.5* (CH$_3$), −0.377 (CH$_3$), 0.76 (CH$_3$), 0.8 (CH$_3$), 1.838 (CH$_2$), 2.162* (CH$_2$), 2.497* (CH$_2$), 2.760* (CH$_2$), 4.717*, 5.556*, 9.066 (CH$_2$), 9.462*(CH$_2$), 10.215* (CH$_2$), 10.579**, $^{29}$Si NMR 99.4 MHz, CDCl$_3$ with Cr(acac)$_3$:δ−19.83, −19.43, 7.81, 8.43, 9.05, 9.88. IR (neat liquid on NaCl): cm$^{-1}$ 2975(s); 2900(s), 2875(m), 2800(w), 1900(w), 1700(w), 1609(m), 1550(m), 1445(w), 1405(s), 1261(s), 1138(s), 1065(s), 800(s), 745(s), 725(w), 690(s), 659(w), 637(w), 550(s). C$_{62}$H$_{170}$Si$_{28}$O$_{25}$ calc C 35.42, H 8.15, Si 37.40, O 19.02; found C 35.11, H7.95. Molecular weight calc. 2,102.4180, observed VPO 2,020.

SCHEME 6

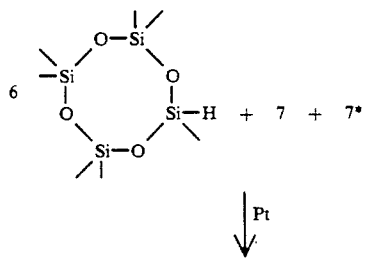

-continued
SCHEME 6
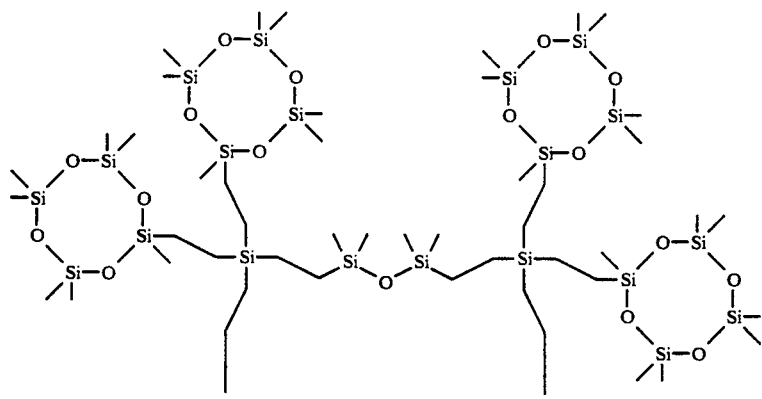
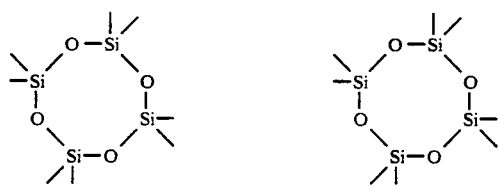
5
+
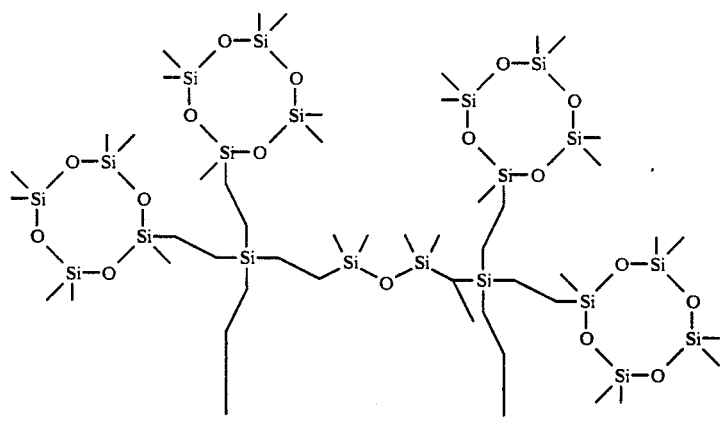
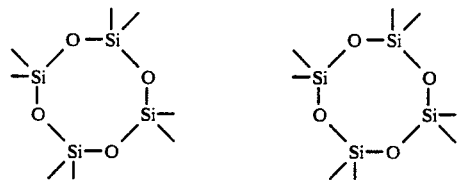
5*
+

SCHEME 6 -continued

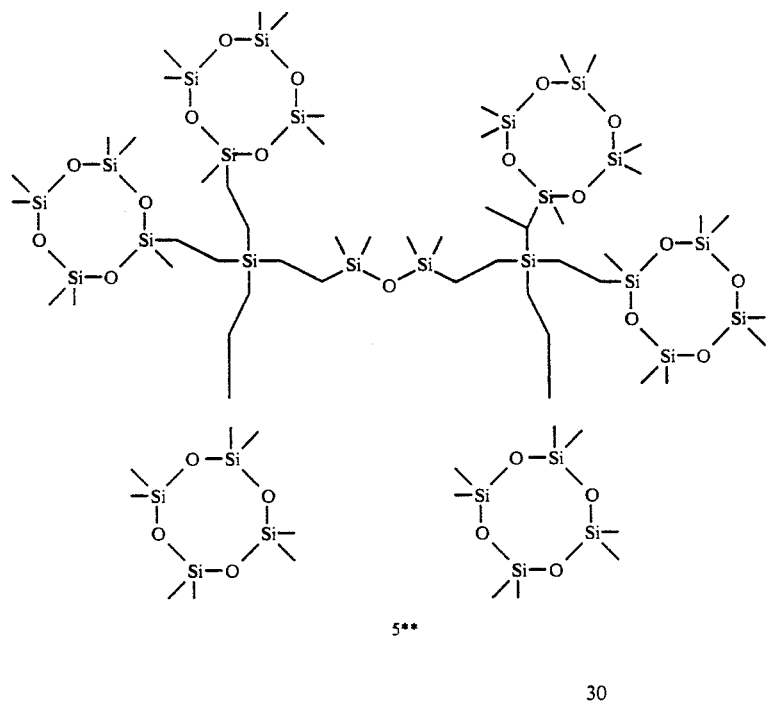

5**

SCHEME 7

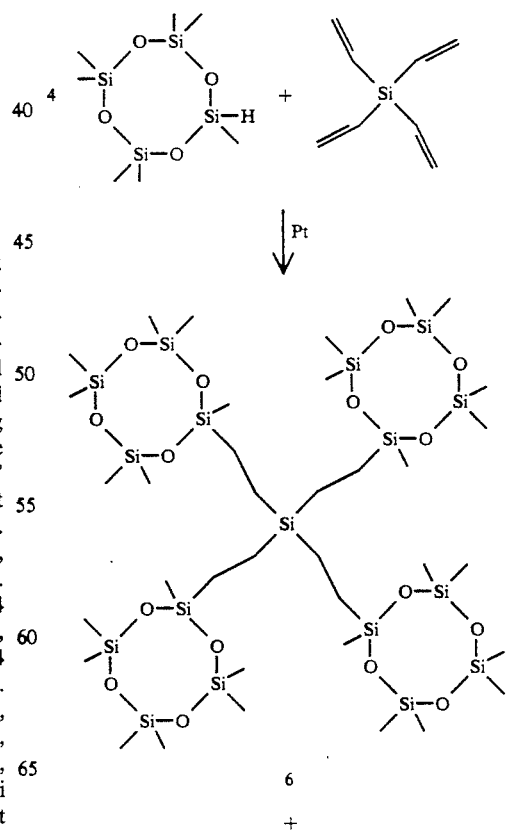

EXAMPLE 6
Preparation of Tetrakis-(2-heptamethylcyclotetrasiloxane-yl-ethyl)silane (6)

A 25 ml round bottomed flask equipped with a reflux condenser was charged with 10 g of 92% pure heptamethylcyclotetrasiloxane (32.6 mmol), 1.1 g of tetravinylsilane (8.1 mmol) and 20 μL platinum-divinylmethyldisiloxane (5% Pt). The mixture was stirred and heated at 70° C. until it turned yellow. An aliquot was removed which indicated complete conversion of the starting olefin by IR and gas chromatography (Scheme 7). The desired product was distilled from the mixture at 140° C. and 0.2 mm Hg. A yield of 8.2 g (82%) of product was isolated. Waxy crystals which melted at 48°-53° C. formed at room temperature. $^1$H NMR 300 MHz, CDCl$_3$:δ 0.113 (s 84H), 0.450 (s 14.7H), 1 038 (d 1.3H). $^{13}$C NMR 75 MHz, CDCl$_3$:δ−1.639, (CH$_3$), 0.754 (CH$_3$), 0.77 (CH$_3$), 1.840 (CH$_2$), 2,467* (CH$_2$), 4.707*, 8.657*, 9.036 (CH$_2$), 9.382* (CH$_2$). $^{29}$Si NMR 99.4 MHz, CDCl$_3$ with Cr(acac)$_3$:δ−19.76, −19.29, 10.51. IR neat liquid on NaCl: cm$^{-1}$ 2975(s); 2900(s), 2875(m), 1900(w), 1700(W), 1625(m), 1555(m), 1445(w), 1405(s), 1255(s), 1138(s), 1070(s), 800(s), 750(s), 725(w), 700(s), 659(w), 550(s), C$_{36}$H$_{100}$Si$_{17}$O$_{16}$ calc C 34.14, H 7.96, Si 37.70, O 20.21; found C 33.98, H 7.88. Molecular weight calc. 1,266.6384, observed VPO 1,320.

-continued
SCHEME 7

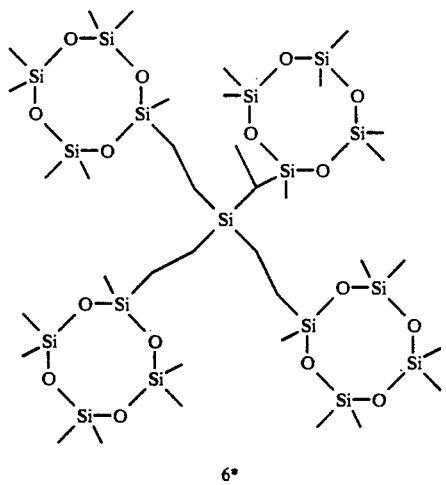

6*

EXAMPLE 7

Preparation of Oxygen-linked bis-Cyclosiloxanes

The preparation of novel oxygen-linked bis-cyclosiloxanes useful for the preparation of thermally reversible rubbers is described as follows.

A 50 mL 3-necked flask fitted with a thermometer, a magnetic stirring bar and a gas inlet was charged with a cyclosiloxane mixture of the following composition: 76.5% by weight heptamethylcyclotetrasiloxane, 12.26% by weight octamethylcyclotetrasiloxane and 11.22% by weight hexamethylcyclotetrasiloxane. After cooling to 0° C., chlorine gas was bubbled through the mixture to convert all of the Si—H bonds to Si—Cl bonds. Complete addition of the chlorine was indicated by the persistence of a slight yellow color. Hydrolysis of the chlorosilanes was carried out by the addition of 2.93 g of water. Nitrogen was then bubbled through the mixture until the mixture was neutral by damp litmus paper. Analysis by gas chromatography indicated that all Si—Cl bonds were converted to Si—O bonds of either silanols or siloxanes. The mixture was then heated to 180°-190° C. for two hours. Vacuum was applied to remove water and the mixture heated for an additional two hours. Complete conversation of silanol to siloxane was indicated. The liquid product consisted of a series of oligomers with the following formula, wherein x is or 2 and n is 1 to 100.

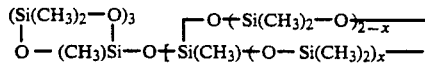

EXAMPLE 8

Preparation of Tetrakis-(heptamethylcyclotetrasiloxane-yl-oxy)silane (8)

A 50 mL 3-necked flask fitted with a thermometer, a magnetic stirring bar and a dean-stark trap with a condenser was charged with 18 grams of heptane and 12 grams of a cyclosiloxane mixture of the following composition: 52.48 by weight hydroxyheptamethylcyclotetrasiloxane, 38.4% by weight octamethylcyclotetrasiloxane and 4.4% by weight bis-heptamethylcyclotetrasiloxane-yl-oxide. The mixture was heated for 45 minutes at 100° C. to remove water which was collected with a dean-stark trap. The mixture was cooled to 90° C., the trap removed and 0.77 g of tetrakis-(dimethylamino)silane was added. The mixture was refluxed for two hours at 106° C. when a gas chromatographic analysis indicated that all of the tetrakis-(dimethylamino)silane was consumed. The lower boiling materials were distilled from the flask under vacuum. The compound tetrakis (heptamethylcyclotetrasiloxane-yl-oxy)silane (8), with the structure

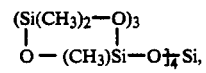

remained and was characterized by proton and silicon-29 NMR spectroscopy.

EXAMPLE 9

Living Rubber Cured From Tris-(2-heptamethylcyclotetrasiloxane-yl-ethyl)methylsilane and Octamethylcyclotetrasiloxane with Trifluoromethane Sulfonic Acid A mixture of 1.93 g of octamethylcyclotetrasiloxane and 0.01 g of tris-(2-heptamethylcyclotetrasiloxane-ethyl)methylsilane and 0.6 g of a fumed silica filler in a 5 dram Polyethylene vial was shaken rapidly with 5 μL of trifluoromethane sulfonic acid. After 30 seconds the mixture was poured onto a teflon sheet. The mixture cured on the surface in less than 10 seconds and remain liquefied inside. At this state, nitrogen gas was introduced inside the curing rubber by a needle. The rubber was inflated and remained as an inflated ball after removal of the needle, as the needle hole healed. After 3 hours the cured rubber was liquefied on the surface when it was heated to 90° C. for 2 minutes. Once it had cooled sufficiently to touch, a finger was pressed to and held on the warm surface until it had cooled to room temperature. The rubber contained a fine impression of the finger print.

The living rubber prepared according to Example 9 was torn into several pieces which were placed on a watch glass, and heat was applied with a heating gun until the rubber melted. The rubber combined into a single piece without noticeable defects or color change. Another piece of rubber was torn and the two fresh surfaces were pressed firmly together and permitted to stand for eight hours. The tear was healed at this point with the strength of the fractured site equivalent to that of the other portions of the network.

The living rubber was selectively "killed" by dusting MgO power onto the external surface. After a period of a few minutes the Mgo was washed from the surface of the rubber with a stream of water and the rubber was heated. The rubber liquefied in the internal region but not on the external surface.

In order to verify that the rubbers were formed via covalent crosslinks, swelling tests were carried out with different solvents. A 0.35 g portion of the rubber was placed into boiling water for 10 hours. The rubber was not swollen and maintained the shape it had prior to

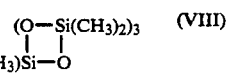 (VIII)

placement in the boiling water. The rubber swelled from 0.48 mL to 4.02 mL when placed in heptane for 4 days and remained that size and shape in heptane for an additional month. The rubber also was placed into an equal volume of octamethylcyclotetrasiloxane for 10 hours. That swelled rubber was very different from the rubber which was swelled in heptane. The swelled rubber did not show that any liquid remained inside or outside of the rubber, indicating that the octamethylcyclotetrasiloxane was incorporated as part of network.

The following comparative Examples 10-13 illustrate the need for a very strong acid catalyst for obtaining formation of a thermally reversible rubber according to the process of the invention.

COMPARATIVE EXAMPLE 10

Curing with Cesium Hydroxide

A 25 mL round-bottom flask was charged with 9.95 g of octamethylcyclotetrasiloxane and 0.05 gram of tris-(2-heptamethylcyclotetrasiloxane-yl-ethyl)methylsilane. The mixture was stirred at room temperature for one hour and 0.02 g of cesium hydroxide was then added into the mixture with stirring. The mixture was then heated at 50° C. Gelation was observed after one hour. This rubber was heated up to 250° C. Thermal reversibility was not observed. The gel never became liquid.

COMPARATIVE EXAMPLE 11

Curing with Sulfuric Acid

A 25 mL round-bottom flask was charged with 9.95 g of octamethylcyclotetrasiloxane and 0.05 g of tris-(2-heptamethylcyclotetrasiloxane-yl-ethyl)methylsilane. The mixture was stirred at room temperature for one hour and 0.02 g of concentrated sulfuric acid was then added into the mixture with stirring. The mixture was then heated at 50° C. Gelation was observed after three hours. This rubber was heated up to 250° C. Thermal reversibility was not observed. The gel never became liquid.

COMPARATIVE EXAMPLE 12

Curing with $P(NH_3)Cl_3$

A 25 mL round-bottom flask was charged with 9.95 g of octamethylcyclotetrasiloxane and 0.05 g of tris-(2-heptamethylcyclotetrasiloxane-yl-ethyl)methylsilane. The mixture was stirred at room temperature for one hour and 0.05 g of $P(NH_3)Cl_5$, which was prepared from $PCl_5$, $FeCl_3$, and $NH_4Cl$ in hexane was then added into the mixture with stirring. Gelation was observed after one hour. This rubber was heated up to 250° C. Thermal reversibility was not observed. The gel never became liquid.

COMPARATIVE EXAMPLE 13

Curing with Tetrabutylammonium Fluoride

A 25 mL round-bottom flask was charged With 9.95 g of octamethylcyclotetrasiloxane and 0.05 g of tris-(2-heptamethylcyclotetrasiloxane-yl-ethyl)-methylsilane. The mixture was stirred at room temperature for one hour and 0.05 g of a 1M solution of tetrabutylammonium fluoride was added into the mixture with stirring. The mixture was heated at 70° C. Gelation was observed after 10 minutes. This rubber was slowly heated from room temperature to 250° C. The network softened and appeared to begin to liquify when the temperature exceeded 100° C. The rubber was cooled and reheated up to 250° C. On the second heating no evidence of thermal reversibility was observed.

TABLE 1

| Ex. | Compound 2 (grams) | Octamethylcyclo-tetrasiloxane (grams) | $HO_3SCF_3$ (wt. %) |
|---|---|---|---|
| 14 | 0.1860 | 14.8140 | 0.17 |
| 15 | 0.0930 | 14.9070 | 0.17 |
| 16 | 0.0465 | 14.9535 | 0.17 |
| 17 | 0.1860 | 14.8140 | 0.34 |
| 18 | 0.0930 | 14.9070 | 0.34 |
| 19 | 0.0465 | 14.9535 | 0.35 |

EXAMPLES 14-19

Living Rubber Cured From 1,3,5,7-Tetra-(2-heptamethylcyclotetrasiloxane-yl-ethyl)-1,3,5,7-tetramethylcyclotetrasiloxane (2) and Octamethylcyclotetrasiloxane A mixture of 1,3,5,7-tetra-(2-heptamethylcyclotetrasiloxane-yl-ethyl)-1,3,5,7-tetramethylcyclotetrasiloxane (compound 2) and octamethylcyclotetrasiloxane, in the amounts set forth in Table 1, was prepared in a large vial. A one gram portion was removed and placed in a vial. Using a 10 microliter syringe, either 1.0 microliter (0.17 weight percent) or 2.0 microliters (0.34 weight percent) of trifluoromethanesulfonic acid was added to the vial. The vial was capped and shaken. After 30 minutes, a silicone rubber was removed from the vial. After one week, it was placed on a watch glass and heated with a heating gun. The rubber behaved as a liquid after a few minutes of heating. Upon cooling the rubbery state was restored.

TABLE 1

| Ex. | Compound 2 (grams) | Octamethylcyclo-tetrasiloxane (grams) | $HO_3SCF_3$ (wt. %) |
|---|---|---|---|
| 14 | 0.1860 | 14.8140 | 0.17 |
| 15 | 0.0930 | 14.9070 | 0.17 |
| 16 | 0.0465 | 14.9535 | 0.17 |
| 17 | 0.1860 | 14.8140 | 0.34 |
| 18 | 0.0930 | 14.9070 | 0.34 |
| 19 | 0.0465 | 14.9535 | 0.35 |

EXAMPLES 20-25

Living Rubber Cured From 1,1,3,3-Tetra-(2-heptamethylcyclotetrasiloxane-yl-ethyl)-1,3-dimethyldisiloxane (3) and Octamethylcyclotetrasiloxane A mixture of 1,1,3,3-Tetra-(2-heptamethylcyclotetrasiloxane-yl-ethyl)-1,3-dimethyldisiloxane (compound and octamethylcyclotetrasiloxane, in the amounts set forth in Table 2, was prepared in a large vial. A one gram portion was removed and placed in a vial. Using a 10 microliter syringe, either 1.0 microliter (0.17 weight percent) or 2.0 microliters (0.34 weight percent) of trifluoromethanesulfonic acid was added to the vial. The vial was capped and shaken. After 30 minutes, a silicone rubber was removed from the vial. After one week, it was placed on a watch glass and heated with a heating gun. The rubber behaved as a liquid after a few minutes of heating. Upon cooling the rubbery state was restored.

TABLE 2

| Ex. | Compound 3 (grams) | Octamethylcyclo-tetrasiloxane (grams) | $HO_3SCF_3$ (wt. %) |
|---|---|---|---|
| 20 | 0.2688 | 14.7312 | 0.17 |
| 21 | 0.1344 | 14.8656 | 0.17 |
| 22 | 0.0672 | 14.9328 | 0.17 |
| 23 | 0,.2688 | 14.7312 | 0.34 |
| 24 | 0.1344 | 14.8656 | 0.34 |
| 25 | 0.0672 | 14.9328 | 0.34 |

EXAMPLES 26–31

Living Rubber Cured From Tris-(2-heptamethylcyclotetrasiloxane-yl-ethyl)methylsilane (4) and Octamethylcyclotetrasiloxane A mixture of tris-(2-heptamethylcyclotetrasiloxane-yl-ethyl)methylsilane (4) and octamethylcyclotetrasiloxane, in the amounts set forth in Table 3, was prepared in a large vial. A one gram portion was removed and placed in a vial. Using a 10 microliter syringe, either 1.0 microliter (0.17 weight percent) or 2.0 microliters (0.34 weight percent) of trifluoromethanesulfonic acid was added to the vial. The vial was capped and shaken. After 30 minutes, a silicone rubber was removed from the vial. After one week, it was placed on a watch glass and heated with a heating gun. The rubber behaved as a liquid after a few minutes of heating. Upon cooling the rubbery state was restored.

TABLE 3

| Ex. | Compound 4 (grams) | Octamethylcyclo-tetra siloxane (grams) | $HO_3SCF_3H$ (wt. %) |
|---|---|---|---|
| 26 | 0.3246 | 14.6754 | 0.17 |
| 27 | 0.1626 | 14.8368 | 0.17 |
| 28 | 0.0813 | 14.9187 | 0.17 |
| 29 | 0.3246 | 14.6754 | 0.34 |
| 30 | 0.1626 | 14.8368 | 0.34 |
| 31 | 0.0813 | 14.9187 | 0.34 |

EXAMPLES 32–37

Living Rubber Cured From 1,3-Di-{2-[tri-(2-heptamethylcyclotetrasiloxane-yl-ethyl)1-silylethyl}-1,1,3,3-tetramethyldisiloxane (5) and Octamethylcyclotetrasiloxane A mixture of 1,3-di-{2-[tri-(2-heptamethylcyclotetrasiloxane-yl-ethyl)]-silylethyl}-1,1,3,3-tetramethyldisiloxane (5) and octamethylcyclotetrasiloxane, in the amounts set forth in Table 4, was prepared in a large vial. A one gram portion was removed and placed in a vial. Using a 10 microliter syringe, either 1.0 microliter (0.17 weight percent) or 2.0 microliters (0.34 weight percent) of trifluoromethanesulfonic acid was added to the vial. The vial was capped and shaken. After 30 minutes, a silicone rubber was removed from the vial. After one week, it was placed on a watch glass and heated with a heating gun. The rubber behaved as a liquid after a few minutes of heating. Upon cooling the rubbery state was restored.

TABLE 4

| Ex. | Compound 5 (grams) | Octamethylcyclo-tetra siloxane (grams) | $HO_3SCF_3$ (wt. %) |
|---|---|---|---|
| 32 | 0.3030 | 14.6970 | 0.17 |
| 33 | 0.1515 | 14.8485 | 0.17 |
| 34 | 0.0757 | 14.9243 | 0.17 |
| 35 | 0.3030 | 14.6970 | 0.34 |
| 36 | 0.1515 | 14.8485 | 0.34 |
| 37 | 0.0757 | 14.9243 | 0.34 |

EXAMPLES 38–43

Living Rubber Cured From Tetrakis-(2-heptamethylcyclotetrasiloxane-yl-ethyl)-silane (6) and Octamethylcyclotetrasiloxane A mixture of tetrakis-(2-heptamethylcyclotetrasiloxane-yl-ethyl)silane (6) and octamethylcyclotetrasiloxane, in the amounts set forth in Table 5, was prepared in a large vial. A one gram portion was removed and placed in a vial. Using a 10 microliter syringe, either 1.0 microliter (0.17 weight percent) or 2.0 microliters (0.34 weight percent) of trifluoromethanesulfonic acid was added to the vial. The vial was capped and shaken. After 30 minutes, a silicone rubber was removed from the vial. After one week, it was placed on a watch glass and heated with a heating gun. The rubber behaved as a liquid after a few minutes of heating. Upon cooling the rubbery state was restored.

TABLE 5

| Ex. | Compound 6 (grams) | Octamethylcyclo-tetra siloxane (grams) | $HO_3SCF_3$ (wt. %) |
|---|---|---|---|
| 38 | 0.3174 | 14.6830 | 0.17 |
| 39 | 0.1589 | 14.8411 | 0.17 |
| 40 | 0.0795 | 14.9205 | 0.17 |
| 41 | 0.3174 | 14.6830 | 0.34 |
| 42 | 0.1589 | 14.8411 | 0.34 |
| 43 | 0.0795 | 14.9205 | 0.34 |

The present invention may be embodied in other specific forms without departing from the spirit and or essential attributes thereof and, accordingly, reference should be made to the appended claims, rather than to the foregoing specification, as indicating the scope of the invention.

We claim:

1. A process for preparing a thermally reversible rubber comprising reacting a mixture comprising a strong acid catalyst having a $pK_a$ of less than about −9, at least one polycyclosiloxane containing at least one polyfunctional siloxane unit, and at least one polysiloxane selected from the group consisting of linear polydimethylsiloxane polydimethylcyclosiloxane containing from about 6 to about 50 silicon-oxygen bonds, linear or cyclic block copolymer of polydimethylsiloxane and a non-siloxane organic polymer, and linear or cyclic random copolymer of a siloxane of the formula $Si(R)(R^1)O$ wherein R and $R^1$ are different and are selected from the group consisting of hydrogen, $C_1$-$C_{18}$ hydrocarbon and $C_2$-$C_{18}$ hydroxyalkyl, wherein the catalyst comprises from about 0.05 to about 0.5 wt % of the reaction mixture, and the concentration of polyfunctional siloxane units contributed by the polycyclosiloxane to the reaction mixture is at least about two times the catalyst concentration in the reaction mixture, but no more than about 0.27 molar.

2. A process according to claim 1 wherein the catalyst comprises from about 0.1 to about 0.4 wt. % of the reaction mixture.

3. A process according to claim 1 wherein the reaction mixture contains at least one polycyclosiloxane having a tetrafunctional or higher functionality polyfunctional siloxane unit.

4. A process according to claim 3 wherein the reaction mixture contains at least one polycyclosiloxane having a pentafunctional or higher functionality polyfunctional siloxane unit.

5. A process according to claim 3 wherein the reaction mixture comprises about 50–99.5 wt. % of said polycyclosiloxane and about 0.25–50 wt. % of said polysiloxane.

6. A process according to claim 3 wherein the polysiloxane comprises a polydimethylcyclosiloxane containing from about 6 to about 50 silicon-oxygen bonds.

7. A process according to claim 6 wherein the polydimethylcyclosiloxane contains from about 8 to about 24 silicon-oxygen bonds.

8. A process according to claim 7 wherein the polydimethylcyclosiloxane comprises octamethylcyclotetrasiloxane.

9. A process according to claim 1, 3, 6, or 8 wherein the catalyst is trifluoromethanesulfonic acid.

10. A process according to claim 1 wherein the polycyclosiloxane is a compound according to formula I,

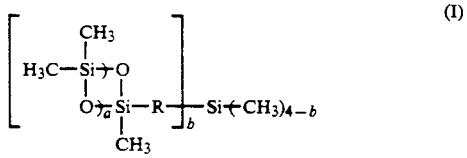

(I)

wherein
R is oxygen, or $C_1$ to $C_{12}$ straight or branched chain alkylenyl,
a is 2 to 20, and
b is 2 to 4.

11. A process according to claim 10 wherein the catalyst is trifluoromethanesulfonic acid.

12. A process according to claim 1 wherein the polycyclosiloxane is a compound according to formula II,

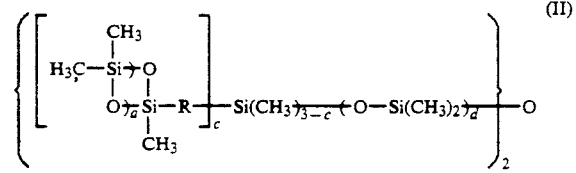

(II)

wherein
R is oxygen, or $C_1$ to $C_{12}$ straight or branched chain alkylenyl,
a is 2 to 20,
c is 1 to 3 and
d is zero to 100.

13. A process according to claim 12 wherein the catalyst is trifluoromethanesulfonic acid.

14. A process according to claim 1 wherein the polycyclosiloxane is a compound according to formula III,

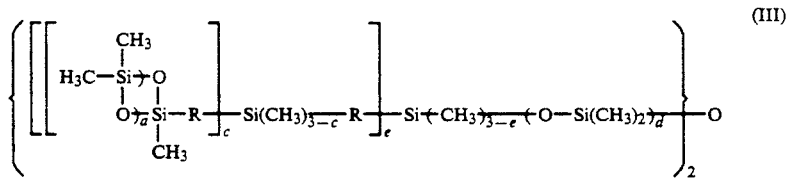

(III)

wherein
R is oxygen, or $C_1$ to $C_{12}$ straight or branched chain alkylenyl,
a is 2 to 20,
c is 1 to 3,
d is zero to 100 and
e is 1 to 3.

15. A process according to claim 14 wherein the catalyst is trifluoromethanesulfonic acid.

16. A process according to claim 1 wherein the polycyclosiloxane is a compound according to formula IV,

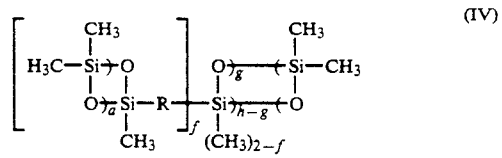

(IV)

wherein
R is oxygen, or $C_1$ to $C_{12}$ straight or branched chain alkylenyl,
a is 2 to 20,
f is 1 or 2,
g is 1 to h and
h is 3 to 20.

17. A process according to claim 16 wherein the catalyst is trifluoromethanesulfonic acid.

18. A process according to claim 1 wherein the polycyclosiloxane is a compound according to formula V,

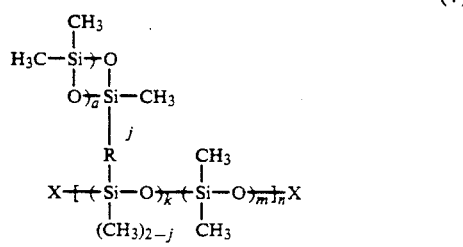

(V)

wherein
R is oxygen, or $C_1$ to $C_{12}$ straight or branched chain alkylenyl, a is 2 to 20,
j is 1 to 2,
m is 1 to 100,
X is hydrogen, $C_1$ to $C_{12}$ straight or branched chain alkyl, $C_1$ to $C_{12}$ straight or branched chain alkoxy, phenyl vinyl or Z, wherein Z is a cyclic moiety according to formula (VII)

$$\begin{array}{c} CH_3 \\ | \\ H_3C-Si-O \\ | \quad | \\ O)_{\overline{a}} Si-R- \\ | \\ CH_3 \end{array} \quad (VII)$$

wherein a and R are defined as above, provided:
when X is Z:
  k is 1 to 100 and n is 1 to 100;
when X is other than Z:
  k is 1 to 100 and
  n is 1 to 100, except that when k is 1 or 2, n must be greater than 2, and when n is 1 or 2, k must greater than 2;
Y is methyl or Z;
p is 1 or 2;
q is zero to r;
r is 1 to 18; and
t is zero to 100.

19. A process according to claim 18 wherein the catalyst is trifluoromethanesulfonic acid.

20. A process according to claim 1 wherein the polycyclosiloxane is a compound according to formula VI, (VI)

[structure VI with CH_3, Si, O, R groups as shown]

wherein
R is oxygen, or $C_1$ to $C_{12}$ straight or branched chain alkylenyl,
a is 2 to 20,
Y is methyl or Z, wherein Z is a cyclic moiety according to formula (VII)

$$\begin{array}{c} CH_3 \\ | \\ H_3C-Si-O \\ | \quad | \\ O)_{\overline{a}} Si-R- \\ | \\ CH_3 \end{array} \quad (VII)$$

wherein a and R are defined as above,
p is 1 or 2,
q is zero to r,
r is 1 to 18, and
t is zero to 100.

21. A process according to claim 20 wherein the catalyst is trifluoromethanesulfonic acid.

22. A process according to claim 20 wherein the polycyclosiloxane is a compound according to formula VIII, wherein x is 1 or 2, and n is 1 to 100:

$$\begin{array}{c} (Si(CH_3)_2-O)_3 \\ | \\ O-(CH_3)Si-O\{Si(CH_3)\{-O-Si(CH_3)_2)_x-Si(CH_3)-O\}_{\overline{n}}(CH_3)Si-O \end{array} \quad \begin{array}{c} [-O\{Si(CH_3)_2-O\}_{\overline{2-x}}] \end{array} \quad \begin{array}{c} (O-Si(CH_3)_2)_3 \\ | \quad | \end{array} \quad (VIII)$$

23. A process according to claim 22 wherein the catalyst is trifluoromethanesulfonic acid.

24. A process according to claim 12 wherein the polycyclosiloxane is 1,3-di(2-heptamethylcyclotetrasiloxane-yl-ethyl)-1,1,3,3-tetramethyldisiloxane.

25. A process according to claim 16 wherein the polycyclosiloxane is 1,3,5,7-tetra-(2-heptamethylcyclotetrasiloxane-yl-ethyl)-1,3,5,7-tetramethylcyclotetrasiloxane.

26. A process according to claim 12 wherein the polycyclosiloxane is 1,3,3,3-tetra-(2-heptamethylcyclotetrasiloxane-yl-ethyl)-1,3-dimethyldisiloxane.

27. A process according to claim 10 wherein the polycyclosiloxane is tris-(2-heptamethylcyclotetrasiloxane-yl-ethyl)-methylsilane.

28. A process according to claim 14 wherein the polycyclosiloxane is 1,3-di-{2-[tri-(2-heptamethylcyclotetrasiloxane-yl-ethyl)]-silylethyl}-1,1,3,3-tetramethyldisiloxane.

29. A process according to claim 10 wherein the polycyclosiloxane is tetrakis-(2-heptamethylcyclotetrasiloxane-yl-ethyl)silane.

30. A process according to claim 10 wherein the polycyclosiloxane is tetrakis-(2-heptamethylcyclotetrasiloxane-yl-oxy)silane.

31. A composition curable to a thermally reversible rubber comprising
  a strong acid catalyst having a $pK_a$ of less than about −9, at least one polycyclosiloxane containing at least one polyfunctional siloxane unit, and at least one polysiloxane selected from the group consisting of
  linear polydimethylsiloxane,
  polydimethylcyclosiloxane containing from about 6 to about 50 silicon-oxygen bonds,
  linear or cyclic block copolymer of polydimethyl siloxane and a non-siloxane organic polymer, and
  linear or cyclic random copolymer of a siloxane of the formula $Si(R)(R^1)O$ wherein R and $R^1$ are different and are selected from the group consisting of hydrogen, $C_1$-$C_{18}$ hydrocarbon and $C_2$-$C_{18}$ hydroxyalkyl,
wherein
  the catalyst comprises from about 0.05 to about 0.5 wt % of the composition, and the concentration of polyfunctional siloxane units contributed by the polycyclosiloxane to the composition is at least about two times the catalyst concentration in the composition, but no more than about 0.27 molar.

32. A composition according to claim 31 wherein the catalyst comprises from about 0.1 to about 0.4 wt. %

33. A composition according to claim 31 Comprising at least one polycyclosiloxane having a tetrafunctional or higher functionality polyfunctional siloxane unit.

34. A composition according to claim 33 comprising at least one polycyclosiloxane having a pentafunctional or higher functionality polyfunctional siloxane unit.

35. A composition according to claim 33 comprising about 50–99.5 wt. % of said polysiloxane and about 0.25–50 wt. % of said polycyclosiloxane.

36. A composition according to claim 33 wherein the polysiloxane comprises a polydimethylcyclosiloxane containing from about 6 to about 50 silicon-oxygen bonds.

37. A composition according to claim 36 wherein the polydimethylcyclosiloxane contains from about 8 to about 24 silicon-oxygen bonds.

38. A composition according to claim 37 wherein the polydimethylcyclosiloxane comprises octamethylcyclotetrasiloxane.

39. A composition according to claim 31, 33, 36 or 38 wherein the catalyst is trifluoromethanesulfonic acid.

40. A composition according to claim 31 wherein the polycyclosiloxane is a compound according to formula I, $$\left[ \begin{array}{c} CH_3 \\ | \\ H_3C-Si+O \\ | \ | \\ O \overline{)_a} Si-R \\ | \\ CH_3 \end{array} \right]_b Si(CH_3)_{4-b}$$ (I)

wherein
R is oxygen, or $C_1$ to $C_{12}$ straight or branched chain alkylenyl,
a is 2 to 20, and
b is 2 to 4.

41. A composition according to claim 40 wherein R is $C_2$ to $C_8$ alkylene, and a is 2 to 8.

42. A composition according to claim 41 wherein the catalyst is trifluoromethanesulfonic acid.

43. A composition according to claim 31 wherein the polycyclosiloxane is a compound according to formula II, $$\left\{ \left[ \begin{array}{c} CH_3 \\ | \\ H_3C-Si+O \\ | \ | \\ O \overline{)_a} Si-R \\ | \\ CH_3 \end{array} \right]_c Si(CH_3)_{3-c} + O-Si(CH_3)_2 \overline{)_d} \right\}_2 O$$ (II)

wherein
R is oxygen, or $C_1$ to $C_{12}$ straight or branched chain alkylenyl,
a is 2 to 20,
c is 1 to 3 and
d is zero to 100.

44. A composition according to claim 43 wherein R is $C_2$ to $C_8$ alkylene, and a is 2 to 8.

45. A composition according to claim 44 wherein the catalyst is trifluoromethanesulfonic acid.

46. A composition according to claim 31 wherein the polycyclosiloxane is a compound according to formula III, $$\left\{ \left[ \begin{array}{c} CH_3 \\ | \\ H_3C-Si+O \\ | \ | \\ O \overline{)_a} Si-R \\ | \\ CH_3 \end{array} \right]_c Si(CH_3)_{3-c}-R \right]_e Si(CH_3)_{3-e} + O-Si(CH_3)_2 \overline{)_d} \right\}_2 O$$ (III)

wherein
R is oxygen, or $C_1$ to $C_{12}$ straight or branched chain alkylenyl,
a is 2 to 20,
c is 1 to 3,
d is zero to 100 and
e is 1 to 3.

47. A composition according to claim 46 wherein R is $C_2$ to $C_8$ alkylene, and a is 2 to 8.

48. A composition according to claim 47 wherein the catalyst is trifluoromethanesulfonic acid.

49. A composition according to claim 31 wherein the polycyclosiloxane is a compound according to formula IV, $$\left[ \begin{array}{cc} CH_3 & CH_3 \\ | & | \\ H_3C-Si+O & O \overline{)_g} Si-CH_3 \\ | \ | & | \ | \\ O \overline{)_a} Si-R & Si \overline{)_{h-g}} O \\ | & | \\ CH_3 & (CH_3)_{2-f} \end{array} \right]_f$$ (IV)

wherein
R is oxygen, or $C_1$ to $C_{12}$ straight or branched chain alkylenyl,
a is 2 to 20,
f is 1 or 2,
g is 1 to h and
h is 3 to 20.

50. A composition according to claim 49 wherein R is $C_2$ to $C_8$ alkylene, a is 2 to 8, and h is 3 to 8.

51. A composition according to claim 50 wherein the catalyst is trifluoromethanesulfonic acid.

52. A composition according to claim 31 wherein the polycyclosiloxane is a compound according to formula V,

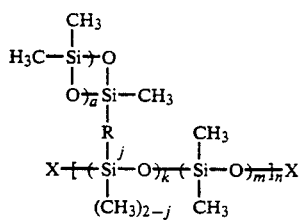
(V)

wherein
R is oxygen, or $C_1$ to $C_{12}$ straight or branched chain alkylenyl,
a is 2 to 20,
j is 1 to 2,
m is 1 to 100,
X is hydrogen, $C_1$ to $C_{12}$ straight or branched chain alkyl, $C_1$ to $C_{12}$ straight or branched chain alkoxy, phenyl vinyl or Z, wherein Z is a cyclic moiety according to formula (VII)

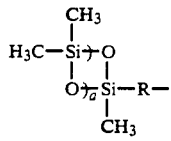
(VII)

wherein a and R are defined as above, provided:
when X is Z:
  k is 1 to 100 and
  n is 1 to 100;
when X is other than Z:
  k is 1 to 100 and
  n is 1 to 100, except that when k is 1 or 2, n must be greater than 2, and when n is 1 or 2, k must be greater than 2;
Y is methyl or Z;
p is 1 or 2;
q is zero to r;
r is 1 to 18; and
t is zero to 100.

53. A composition according to claim 52 wherein R is $C_2$ to $C_8$ alkylene, and a is 2 to 8.

54. A composition according to claim 52 wherein the catalyst is trifluoromethanesulfonic acid.

55. A composition according to claim 31 wherein the polycyclosiloxane is a compound according to formula VI,

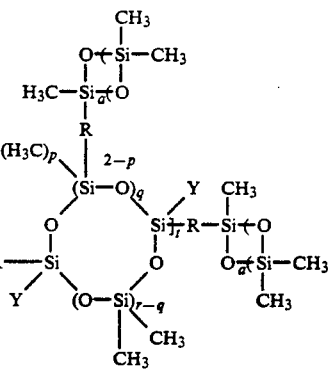
(VI)

wherein
R is oxygen, or $C_1$ to $C_{12}$ straight or branched chain alkylenyl,
a is 2 to 20,
Y is methyl or Z, wherein Z is a cyclic moiety according to formula (VII)

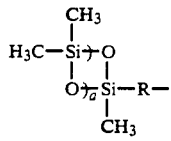
(VII)

wherein a and R are defined as above,
p is 1 or 2,
q is zero to r,
r is 1 to 18, and
t is zero to 100.

56. A composition according to claim 55 wherein R is $C_2$ to $C_8$ alkylene, and a is 2 to 8.

57. A composition according to claim 56 wherein the catalyst is trifluoromethanesulfonic acid.

58. A composition according to claim 31 wherein the polycyclosiloxane is a compound according to formula VIII, wherein x is 1 or 2, and n is 1 to 100:

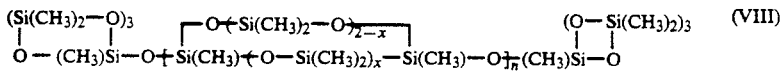

(VIII)

59. A composition according to claim 58 wherein the catalyst is trifluoromethanesulfonic acid.

60. A composition according to claim 44 wherein the polycyclosiloxane is 1,3-di(2-heptamethylcyclotetrasiloxane-yl-ethyl)-1,1,3,3-tetramethyldisiloxane.

61. A composition according to claim 50 wherein the polycyclosiloxane is 1,3,5,7-tetra-(2-heptamethylcyclotetrasiloxane-yl-ethyl)-1,3,5,7-tetramethylcyclotetrasiloxane.

62. A composition according to claim 44 wherein the polycyclosiloxane is 1,3,3,3-tetra-(2-heptamethylcyclotetrasiloxane-yl-ethyl)-1,3-dimethyldisiloxane.

63. A composition according to claim 31 wherein the polycyclosiloxane is tris-(2-heptamethylcyclotetrasiloxane-yl-ethyl)-methylsilane.

64. A composition according to claim 47 wherein the polycyclosiloxane is 1,3-di-{2-[tri-(2-heptamethylcyclotetra-siloxane-yl-ethyl)]-silylethyl}-1,1,3,3-tetramethyldisiloxane.

65. A composition according to claim 41 wherein the polycyclosiloxane is tetrakis-(2-heptamethylcyclotetrasiloxane-yl-ethyl)silane.

66. A composition according to claim 40 wherein the polycyclosiloxane is tetrakis-(2-heptamethylcyclotetrasiloxane-yl-oxy)silane.

67. A process according to claim 1 wherein the polycyclosiloxane contains no cyclosiloxy rings smaller than tetrasiloxyl rings.

68. A process according to claim 3 wherein the polycyclosiloxane contains no cyclosiloxy rings smaller than tetrasiloxyl rings.

69. A composition according to claim 31 wherein the polycyclosiloxane contains no cyclosiloxane rings smaller than tetrasiloxyl rings.

70. A composition according to claim 33 wherein the polycyclosiloxane contains no cyclosiloxane rings smaller than tetrasiloxyl rings.

* * * * *